(12) United States Patent
McArthur

(10) Patent No.: US 9,315,568 B2
(45) Date of Patent: *Apr. 19, 2016

(54) CADHERIN-11 EC1 DOMAIN ANTAGONISTS FOR TREATING INFLAMMATORY JOINT DISORDERS

(71) Applicant: Adheron Therapeutics, Inc., Berkeley, CA (US)

(72) Inventor: James G. McArthur, Concord, MA (US)

(73) Assignee: ADHERON THERAPEUTICS, INC., Berkeley, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 14/070,106

(22) Filed: Nov. 1, 2013

(65) Prior Publication Data

US 2014/0120104 A1 May 1, 2014

Related U.S. Application Data

(63) Continuation of application No. 12/811,921, filed as application No. PCT/US2009/000162 on Jan. 9, 2009, now Pat. No. 8,591,888.

(60) Provisional application No. 61/010,734, filed on Jan. 11, 2008.

(51) Int. Cl.
| | |
|---|---|
| C07K 16/00 | (2006.01) |
| C07K 16/28 | (2006.01) |
| A61K 39/395 | (2006.01) |
| C07K 16/18 | (2006.01) |
| A61K 31/519 | (2006.01) |
| A61K 45/06 | (2006.01) |
| A61K 38/00 | (2006.01) |

(52) U.S. Cl.
CPC ............... *C07K 16/18* (2013.01); *A61K 31/519* (2013.01); *A61K 39/3955* (2013.01); *A61K 45/06* (2013.01); *C07K 16/28* (2013.01); *A61K 38/00* (2013.01); *C07K 2317/34* (2013.01); *C07K 2317/76* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 5,859,205 A | 1/1999 | Adair et al. | |
| 6,358,920 B1 | 3/2002 | Blaschuk et al. | |
| 6,433,149 B1 | 8/2002 | Blaschuk et al. | |
| 6,472,367 B1 | 10/2002 | Blaschuk et al. | |
| 6,569,996 B1 | 5/2003 | Blaschuk et al. | |
| 6,572,857 B1 | 6/2003 | Casimiro et al. | |
| 6,593,297 B2 | 7/2003 | Blaschuk et al. | |
| 6,638,911 B1 | 10/2003 | Blaschuk et al. | |
| 6,680,175 B2 | 1/2004 | Blaschuk et al. | |
| 6,682,901 B2 | 1/2004 | Blaschuk et al. | |
| 6,787,136 B1 | 9/2004 | Brenner et al. | |
| 6,962,969 B2 | 11/2005 | Blaschuk et al. | |
| 7,972,846 B2 | 7/2011 | McArthur | |
| 8,455,249 B2 * | 6/2013 | Aburatani et al. | ............ 435/344 |
| 8,591,888 B2 | 11/2013 | McArthur | |
| 8,940,300 B2 * | 1/2015 | McArthur | .................. 424/133.1 |
| 2003/0096746 A1 | 5/2003 | Blaschuk et al. | |
| 2003/0229199 A1 | 12/2003 | Blaschuk et al. | |
| 2004/0110755 A1 | 6/2004 | Simianer et al. | |
| 2004/0229811 A1 | 11/2004 | Blaschuk et al. | |
| 2004/0248219 A1 | 12/2004 | Blaschuk et al. | |
| 2004/0248220 A1 | 12/2004 | Blaschuk et al. | |
| 2005/0215482 A1 | 9/2005 | Blaschuk et al. | |
| 2008/0076739 A1 | 3/2008 | Viallet | |
| 2009/0253200 A1 | 10/2009 | McArthur | |
| 2011/0045003 A1 | 2/2011 | McArthur | |
| 2013/0189251 A1 | 7/2013 | McArthur | |
| 2015/0132305 A1 | 5/2015 | McArthur | |

FOREIGN PATENT DOCUMENTS

| | | |
|---|---|---|
| WO | WO 99/57149 A1 | 11/1999 |
| WO | WO 01/17557 A1 | 3/2001 |
| WO | WO 2004/048411 A2 | 6/2004 |
| WO | WO 2009/089062 A2 | 7/2009 |
| WO | WO 2009/101059 A2 | 8/2009 |
| WO | WO 2012/009631 A1 | 1/2012 |

OTHER PUBLICATIONS

Chappuis-Flament, S., et al., "Multiple Cadherin Extracellular Repeats Mediate Homophilic Binding and Adhesion," *The Journal of Cell Biology* 154(1):231-243 (2001).

Hoet, R.M., et al., "Generation of High-affinity Human Antibodies by Combining Donor-derived and Synthetic Complementarity-determining-region Diversity," *Nature Biotechnology* 23(3):344-348 (2005).

Kiener, H.P., et al. "Building the Synovium: Cadherin-11 Mediates Fibroblast-like Synoviocyte Cell-to-Cell Adhesion," *Arthritis Res. Ther.* 7:49-54 (2005).

Kiener, H.P., et al. "Cadherin-11 Induces Rheumatoid Arthritis Fibroblast-Like Synoviocytes to Form Lining Layers in Vitro," *American Journal of Pathology* 168(5):1486-1499 (2006).

Lee, D.M., et al., "Cadherin-11 in Synovial Lining Formation and Pathology in Arthritis," *Science* 315:1006-1010 (2007).

May, C., et al., "Identification of a Transiently Exposed VE-cadherin Epitope that Allows for Specific Targeting of an Antibody to the Tumor Neovasculature," *Blood* 105(11):4337-4344 (2005).

Okazaki, M., et al., "Molecular Cloning and Characertization of OB-cadherin, a New Member of Cadherin Family Expressed in Osteoblasts," *The Journal of Biological Chemistry* 269(16):12092-12098 (1994).

(Continued)

*Primary Examiner* — Maher Haddad
(74) *Attorney, Agent, or Firm* — Hamilton, Brook, Smith & Reynolds, P.C.

(57) ABSTRACT

The present invention relates to Cadherin-11 antagonists and compositions comprising Cadherin-11 antagonists. The invention also relates to methods for treating inflammatory joint disorders, such as rheumaotid arthritis, in a mammalian subject by administering a therapeutically effective amount of a Cadherin-11 antagonist.

17 Claims, 32 Drawing Sheets

(56) References Cited

OTHER PUBLICATIONS

Patel, S.D., et al., "Type II Cadherin Ectodomain Structures: Implications for Classical Cadherin Specificity," *Cell* 124:1255-1268 (2006).
Rauchenberger, R., et al., "Human Combinatorial Fab Library Yielding Specific and Functional Antibodies Against the Human Fibroblast Growth Factor Receptor 3," *The Journal of Biological Chemistry* 278(40):38194-38205 (2003).
Shan, W., et al., "The Minimal Essential Unit for Cadherin-mediated Intercellular Adhesion Comprises Extracellular Domains 1 and 2," *The Journal of Biological Chemistry* 279(53):55914-55923 (2004).
Valencia, X., et al., "Cadherin-11 Provides Specific Cellular Adhesion Between Fibroblast-like Synoviocytes,"*J. Exp. Med.* 200(12):1673-1679 (2004).
Zhu, B., et al., "Functional Analysis of the Structural Basis of Homophilic Cadherin Adhesion," *Biophysical Journal* 84:4033-4042 (2003).
Invitation to Pay Additional Fees and, Where Applicable, Protest Fee—Annex to Form PCT/ISA/206 Communication Relating to the Results of the Partial International Search Report from PCT/US2009/000162, "Cadherin-11 EC1 Domain Antagonists for Treating Inflammatory Joint Disorders," 10 pages, Dated Jun. 17, 2009.
International Search Report from International Application No. PCT/US2009/000162; "Cadherin-11 EC1 Domain Antagonists for Treating Inflammatory Joint Disorders," 11 pages, Dated: Aug. 5, 2009.
Written Opinion of the International Searching Authority from International Application No. PCT/US2009/000162; "Cadherin-11 EC1 Domain Antagonists for Treating Inflammatory Joint Disorders," 10 pages, Date: Aug. 5, 2009.
Notification Concerning Transmittal of International Preliminary Report on Patentability and International Preliminary Report on Patentability in International Application No. PCT/US2009/000162, "Cadherin-11 EC1 Domain Antagonists for Treating Inflammatory Joint Disorders," 11 pages, mailed Jul. 22, 2010.
Geli, V., et al., "Recognition of the Colicin A N-Terminal Eptitope 1C11 in vitro and in vivo in *Escherichia coli* by its Cognate Monoclonal Antibody," *FEMS Microbiology Letters*, 109:335-342 (1993).
Katafiasz, B.J., et al., "Characterization of Cadherin-24, a Novel Alternatively Spliced Type II Cadherin," *The Journal of Biological Chemistry*, 278(30):27513-27519 (2003).
Padlan, E.A., "Anatomy of the Antibody Molecule," *Molecular Immunology*, 31(3):169-217 (1994).
Vajdos, F.F., et al., "Comprehensive Functional Maps of the Antigen-binding Site of an Anti-ErbB2 Antibody Obtained with Shotgun Scanning Mutagenesis," *J. Mol. Biol.*, 320:415-428 (2002).
Office Action of U.S. Appl. No. 12/427,993, "Cadherin-11 Antagonists and Methods for the Treatment of Inflammatory Joint Disorders," Date of Mailing Aug. 10, 2010. *
Reply to Restriction Requirement of U.S. Appl. No. 12/427,993, "Cadherin-11 Antagonists and Methods for the Treatment of Inflammatory Joint Disorders," Date of Mailing Sep. 8, 2010. *
Office Action of U.S. Appl. No. 12/427,993, "Cadherin-11 Antagonists and Methods for the Treatment of Inflammatory Joint Disorders," Date of Mailing Sep. 20, 2010.*

Non-Final Office Action received in U.S. Appl. No. 12/837,110, "Cadherin-11 Antagonists and Methods for the Treatment of Inflammatory Joint Disorders," dated Jan. 9, 2012.*
International Search Report from International Application No. PCT/US2011/044172, "Humanized Antibodies Targeting the EC1 Domain of Cadherin-11 and Related Compositions and Methods," date of mailing Nov. 18, 2011.
Monahan, T.S., et al., "A novel function for cadherin 11/osteoblast-cadherin in vascular smooth muscle cells: Modulation of cell migration and proliferation," *Journal of Vascular Surgery*, 45(3): 581-589 (Mar. 1, 2007).
Baumgartner, W., et al., "Cadherin interaction probed by atomic force microscopy," PNAS, 97(8): 4005-4010 (Apr. 11, 2000).
Renaud-Young, M., and Gallin, W.J., "In the First Extracellular Domain of E-cadherin, Heterophilic Interactions, but Not the Conserved His-Ala-Val Motif, are Required for Adhesion," *The Journal of Biological Chemistry*, 277(42): 39609-39616 (Oct. 18, 2002).
Shapiro, L., et al., "Structural basis of cell-cell adhesion by cadherins," *Nature*, 374(6520):327-337 (Mar. 23, 1995).
Sivasankar, S., et al., "Direct Measurements of Multiple Adhesive Alignments and Unbinding Trajectories between Cadherin Extracellular Domains," *Biophysical Journal*, 80: 1758-1768, (Apr. 2001).
Lederman, S. et al., "A Single Amino Acid Substitution in a Common African Allele of the CD4 Molecule Ablates Binding of the Monoclonal Antibody," *OKT4. Mol Immunol.* 28(11): 1171-81, 1991.
Amendment of U.S. Appl. No. 12/427,993, "Cadherin-11 Antagonists and Methods for the Treatment of Inflammatory Joint Disorders," Date of Mailing: Jan. 20, 2011.
Final Office Action of U.S. Appl. No. 12/427,993, "Cadherin-11 Antagonists and Methods for the Treatment of Inflammatory Joint Disorders," Date of Mailing: Feb. 9, 2011.
Amendment After Final Rejection of U.S. Appl. No. 12/427,993, "Cadherin-11 Antagonists and Methods for the Treatment of Inflammatory Joint Disorders," Date of Mailing: Mar. 15, 2011.
Transmittal of Sequence Listing and Preliminary Amendment in Response to Notice to File Missing Parts of Application of U.S. Appl. No. 12/837,110, "Cadherin-11 Antagonists and Methods for the Treatment of Inflammatory Joint Disorders," Date of Mailing: Oct. 28, 2010.
Restriction Requirement of U.S. Appl. No. 12/837,110, "Cadherin-11 Antagonists and Methods for the Treatment of Inflammatory Joint Disorders," Date of Mailing: Mar. 3, 2011.
Notice of Allowance and Fees Due, U.S. Appl. No. 12/427,993, "Cadherin-11 Antagonists and Methods for the Treatment of Inflammatory Joint Disorders," Date of Mailing: Mar. 28, 2011.
Ding, M. et al., "Partial Characterization of the MPM-2 Phosphoepitope," *Exp. Cell Res.*, 231(1): 3-13 (1997).
Gonzales, N. R., et al., "Minimizing the Immunogenicity of Antibodies for Clinical Application," *Tumor Biol.* (2005) 26:31-43.
International Preliminary Report on Patentability for Int'l Application No. PCT/US2011/044172; Date of Issuance: Jan. 15, 2013.
Office Action from U.S. Appl. No. 13/810,018; Dated: Jun. 27, 2014; entitled "Humanized Antibodies Targeting the EC1 Domain of Cadherin-11 and Related Compositions and Methods."
Written Opinion for Int'l Application No. PCT/US2011/044172; Date Mailed: Nov. 18, 2011; entitled "Humanized Antibodies Targeting the EC1 Domain of Cadherin-11 and Related Compositions and Methods."

* cited by examiner

| | | | | | |
|---|---|---|---|---|---|
| Human Cad-11 | GWVWN | QFFVI | EEYTG PDPVL VGRLH SDIDS GDGN | (SEQ ID NO:3) |
| Human Cad-8 | GWVWN | QMFVL | EEFSG PEPIL VGRLH TDLDP GSKK | (SEQ ID NO:4) |
| Human MN-Cad | SWVWN | QFFVL | EEYTG TDPLY VGKLH SDMDR GDGS | (SEQ ID NO:5) |

FIG. 2

ATGAAGGAGAACTACTGTTTACAAGCCGCCCTGGTGTGCCTGGGCATGCTGTGCCACAGCCATGCC
TTTGCCCCAGAGCGGGGCCACCTGCGGCCCCTCCTTCCATGGGCACCATGAGAAGGGCAAGG
AGGGCAGGTGCTACAGCGCTCCAAGCGTCTGGAACCAGTTCTTCGTGATAGAGGAG
TACACCCGGGCCTGACCCCGTGCTTGTGGGCAGGCTTCATTCAGATATTGACTCTGGTGATGGAACA
TTAAATACATTCTCTCAGGGAAGGAGCTGGAACCATTTTTGTGATTGATGAACAAATCAGGGAACATT
CATGCCACCAAGACGTTGGATCGAGAAGAGAGCCAGTACACGTTGATGGCTCAGGCGGTGGA
CAGGGACACCAATCGGCCACTGGAGCCACCGTCGGAATTCATTGTCAAGGTCCAGAGATCTGTGGA
GTGCCCACCTTGCCCCAGCACCACCTGTGGCAGGACCTTCAGTCTTCCTCTTCCCCCAAAACCCA
AGGACACCCTGAGGTCTCCAGAACCCTGAGGTGCGTGGTGGACGTGAGCCACGA
AGACCCCGAGGTCAAGTTCAACTGGTACGTGGACGGCATGAGGTGCATAATGCCAAGACAAAG
CCACGGGAGGAGCAGTTCAACAGCACGTTCCGTGTGGTCAGCGTCCTCACCGTCGTGCACCAGG
ACTGGCTGAACGGCAAGGAGTACAAGTGCAAGGTCTCCAACAAAGCCCTCCCAGCCCCCATCGA
GAAAACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTACCCCAGCG
ACATCGCCGTGGAGTGGGAGAGCAATGGGCAGCCGGAGAACAACTACAAGACCACCTCCCAT
GCTGGACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACACAGAAGAG
CCTCTCCCTGTCTCCGGGTAAATGAGTGCCACGGGCTAGCTGG (SEQ ID NO:6)

FIG. 8

MKENYCLQAALVCLQGMLCHSHAFAPERRGHLRPSFHGHHEKGKEGQVLQ
RSKRGWVWNQFFVIEEYTGPDPVLVGRLHSDIDSGDGNIKYILSGEGAGTIF
VIDDKSGNIHATKTLDREERAQYTLMAQAVDRDTNRPLEPPSEFIVKVQ
RSVECPPPCPAPPVAGPSVFLFPPKPKDTLMISRTPEVTCVVVDVSHEDPEV
QFNWYVDGMEVHNAKTKPREEQFNSTFRVVSVLTVVHQDWLNGKEYKC
KVSNKGLPAPIEKTISKTKGQPREPQVYTLPPSREEMTKNQVSLTCLVKGF
YPSDIAVEWESNGQPENNYKTTPPMLDSDGSFFLYSKLTVDKSRWQQGN
VFSCSVMHEALHNHYTQKSLSLSPGKVPRLA (SEQ ID NO:7)

FIG. 9

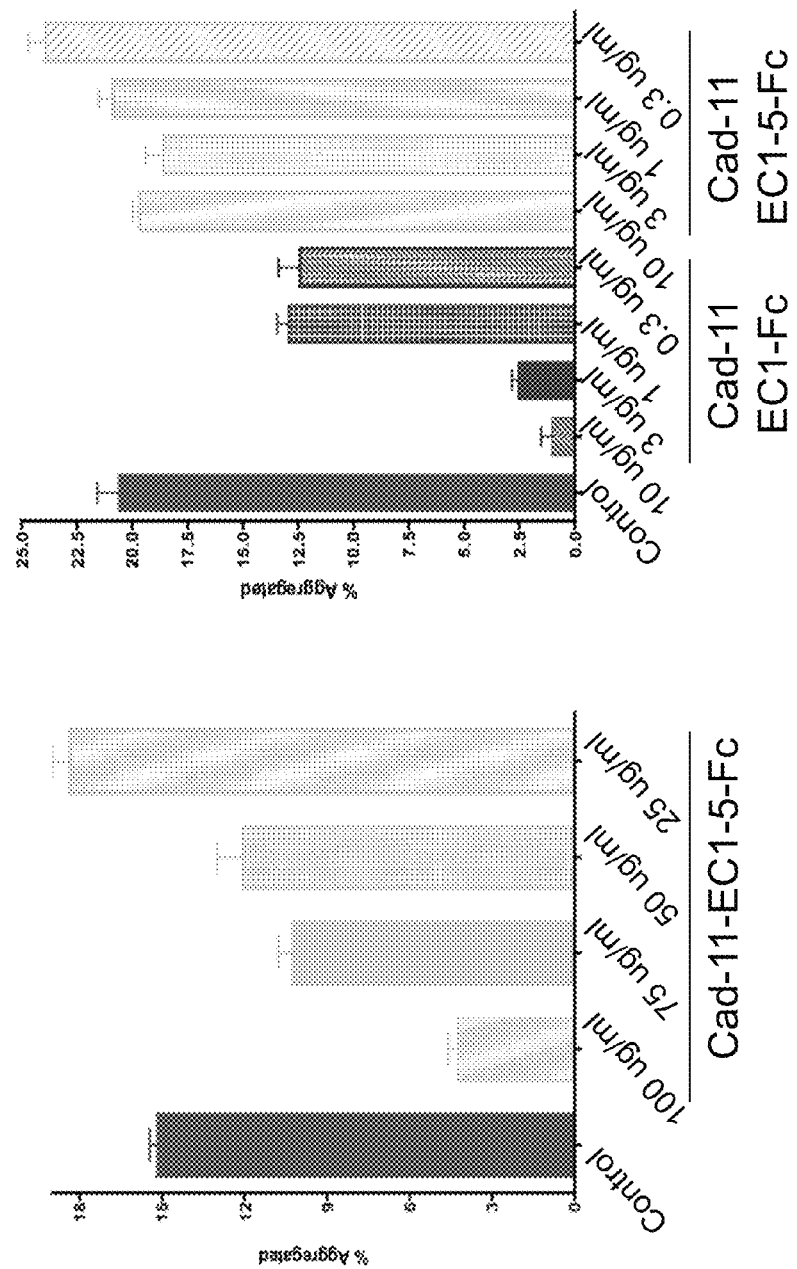

```
   1 agatgccgcg ggggccgctc gcagccgccg ctgacttgtg aatgggaccg ggactggggc
  61 cgggactgac accgcagcgc ttgccctgcg ccagggactg gcggctcgga ggttgcgtcc
 121 accctcaagg gccccagaaa tcactgtgtt ttcagctcag cggccctgtg acattccttc
 181 gtgttgtcat ttgttgagtg accaatcaga tgggtggagt gtgttacaga aattggcagc
 241 aagtatccaa tgggtgaaga agaagctaac tggggacgtg ggcagccctg acgtgatgag
 301 ctcaaccagc agagacattc catcccaaga gaggtctgcg tgacgcgtcc gggaggccac
 361 cctcagcaag accaccgtac agttggtgga agggtgaca gctgcattct cctgtgccta
 421 ccacgtaacc aaaaatgaag gagaactact gtttacaagc cgccctggtg tgcctgggca
 481 tgctgtgcca cagccatgcc tttgcccag agcggcgggg gcacctgcgg ccctccttcc
 541 atgggcacca tgagaagggc aaggagggc aggtgctaca gcgctccaag cgtggctggg
 601 tctggaacca gttcttcgtg atagaggagt acaccggggcc tgaccccgtg cttgtgggca
 661 ggcttcattc agatattgac tctggtgatg ggaacattaa atacattctc tcaggggaag
 721 gagctggaac cattttgtg attgatgaca atcagggaa cattcatgcc accaagacgt
 781 tggatcgaga agagagagcc cagtacacgt tgatggctca ggcggtggac agggacacca
 841 atcggccact ggagccaccg tcggaattca ttgtcaaggt ccaggacatt aatgacaacc
 901 ctccggagtt cctgcacgag acctatcatg ccaacgtgcc tgagaggtcc aatgtgggaa
 961 cgtcagtaat ccaggtgaca gcttcagatg cagatgaccc cacttatgga aatagcgcca
1021 agttagtgta cagtatcctc gaaggacaac cctatttttc ggtggaagca cagacaggta
1081 tcatcagaac agccctaccc aacatggaca gggaggccaa ggaggagtac cacgtggtga
1141 tccaggccaa ggacatgggt ggacatatgg gcggactctc agggacaacc aaagtgacga
1201 tcacactgac cgatgtcaat gacaacccac caaagtttcc gcagagcgta taccagatgt
1261 ctgtgtcaga agcagccgtc cctggggagg aagtaggaag agtgaaagct aaagatccag
1321 acattggaga aaatggctta gtcacataca atattgttga tggagatggt atggaatcgt
1381 ttgaaatcac aacggactat gaaacacagg aggggtgat aaagctgaaa aagcctgtag
1441 attttgaaac caaaagagcc tatagcttga aggtagaggc agccaacgtg cacatcgacc
1501 cgaagtttat cagcaatggc ccttcaagg acactgtgac cgtcaagatc tcagtagaag
1561 atgctgatga gccccctatg ttcttggccc caagttacat ccacgaagtc caagaaaatg
1621 cagctgctgg caccgtggtt gggagagtgc atgccaaaga ccctgatgct gccaacagcc
```

FIG. 14A

```
1681 cgataaggta ttccatcgat cgtcacactg acctcgacag atttttcact attaatccag
1741 aggatggttt tattaaaact acaaaacctc tggatagaga ggaaacagcc tggctcaaca
1801 tcactgtctt tgcagcagaa atccacaatc ggcatcagga agccaaagtc ccagtggcca
1861 ttagggtcct tgatgtcaac gataatgctc ccaagtttgc tgcccttat gaaggtttca
1921 tctgtgagag tgatcagacc aagccacttt ccaaccagcc aattgttaca attagtgcag
1981 atgacaagga tgacacggcc aatggaccaa gatttatctt cagcctaccc cctgaaatca
2041 ttcacaatcc aaatttcaca gtcagagaca accgagataa cacagcaggc gtgtacgccc
2101 ggcgtggagg gttcagtcgg cagaagcagg acttgtacct tctgcccata gtgatcagcg
2161 atggcggcat cccgcccatg agtagcacca cacccctcac catcaaagtc tgcgggtgcg
2221 acgtgaacgg ggcactgctc tcctgcaacg cagaggccta cattctgaac gccggcctga
2281 gcacaggcgc cctgatcgcc atcctcgcct gcatcgtcat tctcctggtc attgtagtat
2341 tgtttgtgac cctgagaagg caaaagaaag aaccactcat tgtctttgag gaagaagatg
2401 tccgtgagaa catcattact tatgatgatg aaggggtgg ggaagaagac acagaagcct
2461 ttgatattgc caccctccag aatcctgatg gtatcaatgg atttatcccc gcaaagaca
2521 tcaaacctga gtatcagtac atgcctagac ctgggctccg gccagcgccc aacagcgtgg
2581 atgtcgatga cttcatcaac acgagaatac aggaggcaga caatgacccc acggctcctc
2641 cttatgactc cattcaaatc tacggttatg aaggcagggg ctcagtggcc gggtccctga
2701 gctccctaga gtcggccacc acagattcag acttggacta tgattatcta cagaactggg
2761 gacctcgttt taagaaacta gcagatttgt atggttccaa agacacttt gatgacgatt
2821 cttaacaata acgatacaaa tttggcctta agaactgtgt ctggcgttct caagaatcta
2881 gaagatgtgt aaacaggtat tttttaaat caaggaaagg ctcatttaaa acaggcaaag
2941 ttttacagag aggatacatt taataaaact gcgaggacat caaagtggta atactgtga
3001 aataccttt ctcacaaaaa ggcaaatatt gaagttgttt atcaacttcg ctagaaaaaa
3061 aaaacacttg gcatacaaaa tatttaagtg aaggagaagt ctaacgctga actgacaatg
3121 aagggaaatt gtttatgtgt tatgaacatc caagtctttc ttcttttta agttgtcaaa
3181 gaagcttcca caaaattaga aaggacaaca gttctgagct gtaatttcgc cttaaactct
3241 ggacactcta tatgtagtgc atttttaaac ttgaaatata taatattcag ccagcttaaa
3301 cccatacaat gtatgtacaa tacaatgtac aattatgtct cttgagcatc aatcttgtta
3361 ctgctgattc ttgtaaatct ttttgcttct actttcatct taaactaata cgtgccagat
```

FIG. 14B

```
3421 ataactgtct tgtttcagtg agagacgccc tatttctatg tcatttttaa tgtatctatt 3481 tgtacaattt taaagttctt attttagtat acgtataaat atcagtattc tgacatgtaa 3541 gaaaatgtta cggcatcaca cttatatttt atgaacattg tactgttgct ttaatatgag 3601 cttcaatata agaagcaatc tttgaaataa aaaagatttt tttttaaaa aaaa (SEQ
ID NO:1)
```

FIG. 14C

```
  1  mkenyclqaa  lvclgmlchs  hafaperrgh  lrpsfhghhe  kgkegqvlqr  skrgwvwnqf
 61  fvieeytgpd  pvlvgrlhsd  idsgdgniky  ilsgegagti  fviddksgni  hatktldree
121  raqytlmaqa  vdrdtnrple  ppsefivkvq  dindnppefl  hetyhanvpe  rsnvgtsviq
181  vtasdaddpt  ygnsaklvys  ilegqpyfsv  eaqtgiirta  lpnmdreake  eyhvviqakd
241  mgghmgglsg  ttkvtitltd  vndnppkfpq  svyqmsvsea  avpgeevgrv  kakdpdigen
301  glvtynivdg  dgmesfeitt  dyetqegvik  lkkpvdfetk  rayslkveaa  nvhidpkfis
361  ngpfkdtvtv  kisvedadep  pmflapsyih  evqenaaagt  vvgrvhakdp  daanspirys
421  idrhtdldrf  ftinpedgfi  kttkpldree  tawlnitvfa  aeihnrhqea  kvpvairvld
481  vndnapkfaa  pyegficesd  qtkplsnqpi  vtisaddkdd  tangprfifs  lppeiihnpn
541  ftvrdnrdnt  agvyarrggf  srqkqdlyll  pivisdggip  pmsstntlti  kvcgcdvnga
601  llscnaeayi  lnaglstgal  iailacivil  lvivvlfvtl  rrqkkepliv  feeedvreni
661  ityddeggge  edteafdiat  lqnpdgingf  iprkdikpey  qymprpglrp  apnsvdvddf
721  intriqeadn  dptappydsi  qiygyegrgs  vagslssles  attdsdldyd  ylqnwgprfk
781  kladlygskd  tfddds (SEQ ID NO: 2)
```

FIG. 15

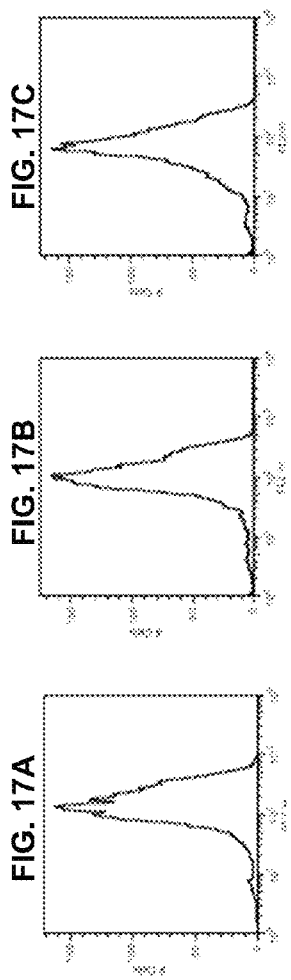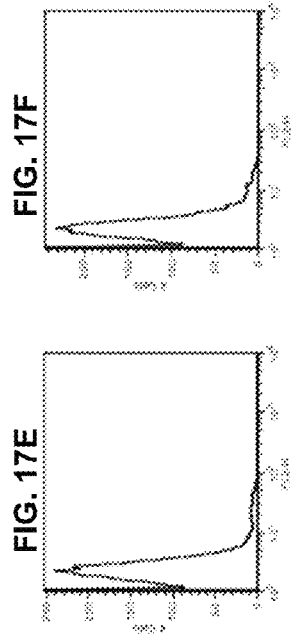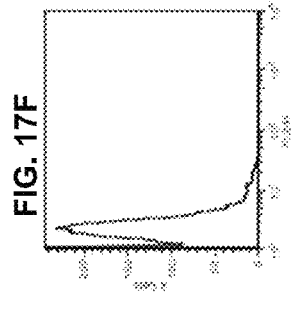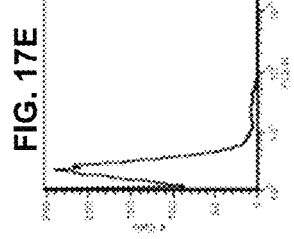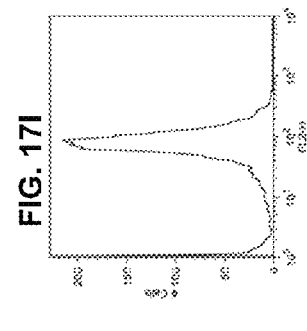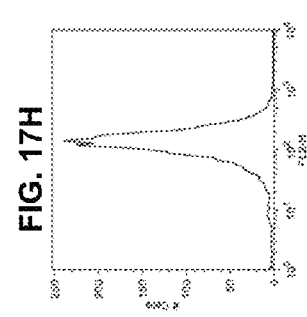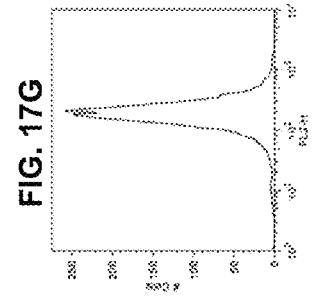

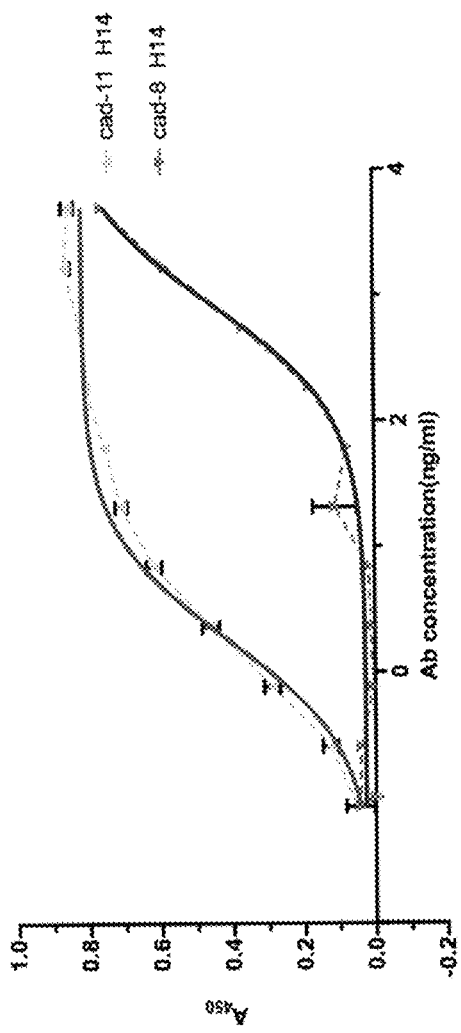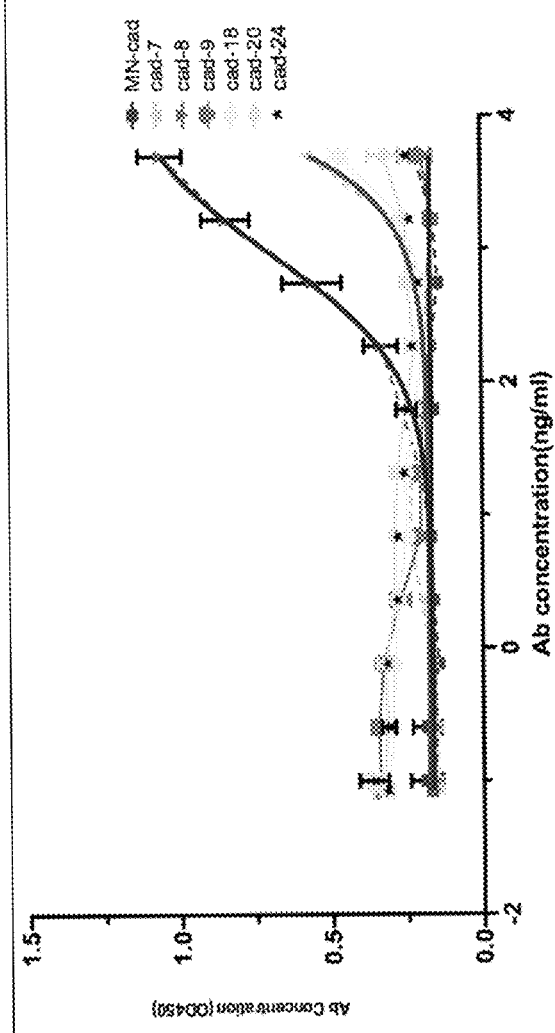
FIG. 19A
FIG. 19B

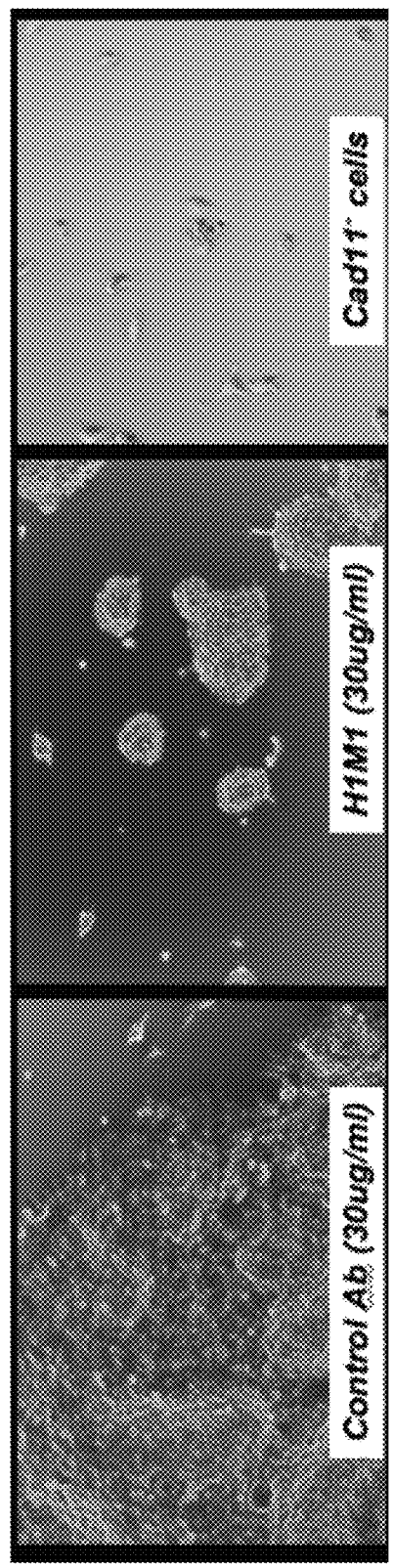

CADHERIN-11 EC1 DOMAIN ANTAGONISTS FOR TREATING INFLAMMATORY JOINT DISORDERS

RELATED APPLICATION(S)

This application is a continuation of U.S. application Ser. No. 12/811,921, now U.S. Pat. No. 8,591,888, which is the U.S. National Stage of International Application No. PCT/US2009/000162, filed on Jan. 9, 2009, published in English, which claims the benefit of U.S. Provisional Application No. 61/010,734, filed on Jan. 11, 2008. The entire teachings of the above applications are incorporated herein by reference.

BACKGROUND OF THE INVENTION

Patients with advanced chronic joint inflammation suffer from severe joint deterioration including bone and cartilage destruction, resulting in long-term pain, deformity, loss of joint function, reduced mobility and shortened life expectancy. Joint inflammation is associated with an increased number of cells and inflammatory substances in the joint, which cause irritation, wearing down of cartilage and swelling of the joint lining. Several different autoimmune disorders are known to trigger inappropriate or misdirected inflammation in a joint, resulting in chronic inflammation in the joints of individuals who suffer from these disorders. Common inflammatory joint disorders include rheumatoid arthritis, psoriatic arthritis, Reiter's syndrome and ankylosing spondylitis.

Rheumatoid arthritis (RA) is the most common form of inflammatory arthritis and is estimated to affect approximately 1 percent of the U.S. population, or about 2.1 million Americans. RA is a chronic disease that is characterized by inflammation of the lining, or synovium, of the joints, and can lead to significant bone and cartilage damage over time. RA is more common in women than in men and as many as 3% of women may develop rheumatoid arthritis in their lifetime. Currently, the cause of RA is unknown.

RA can lead to long-term joint damage, resulting in chronic pain, loss of function and disability. In addition, recent research indicates that people with RA, particularly those whose disease is not well controlled, may have a higher risk for heart disease and stroke. Thus, RA is a major national health burden and there is an urgent need to develop new agents for the prevention and treatment of rheumatoid arthritis, and other inflammatory joint disorders.

SUMMARY OF THE INVENTION

The present invention encompasses, in one embodiment, a Cadherin-11 antagonist that specifically binds an extracellular 1 (EC1) domain of a mammalian Cadherin-11 protein, and inhibits aggregation of cells that express the mammalian Cadherin-11. In a particular embodiment, the Cadherin-11 antagonist is an antibody or an antibody fragment. In another embodiment, the Cadherin-11 antagonist is a fusion protein that comprises the EC1 domain of a Cadherin-11 protein (e.g., SEQ ID NO:3).

In an additional embodiment, the invention relates to methods of treating an inflammatory joint disorder in a mammalian subject (e.g., a human). The method comprises administering to the mammalian subject a therapeutically effective amount of a Cadherin-11 antagonist of the invention, thereby resulting in a desired therapeutic effect in the mammal. In a particular embodiment, the methods of the invention can be used to treat rheumatoid arthritis.

In another embodiment, the invention encompasses a pharmaceutical composition comprising a Cadherin-11 antagonist of the invention and a pharmaceutically-acceptable carrier. In one embodiment, the pharmaceutical composition further comprises a second agent, such as a disease-modifying anti-rheumatic drug or an anti-inflammatory agent.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 is an amino acid sequence alignment of the first 34 amino acids of the EC1 domains of human Cad-11 (SEQ ID NO:3), MN-Cad (SEQ ID NO:4), and Cad-8 (SEQ ID NO:5) that are involved in cadherin binding. Donor sequences containing residues that extend into the pocket of a cadherin counter-receptor are indicated by underlining of the left half of sequence and residues of the pocket sequence are indicated by the underlining of the right half of sequence in SEQ ID NO:3.

μg/ml and 0.1 μg/ml. The EC1-Fc fusion protein inhibited aggregation of 431-D-11 cells at concentrations of 3 μg/ml. In contrast, the anti-GFP Fab failed to inhibit cell aggregation significantly at any of the test concentrations.

Figure 6:
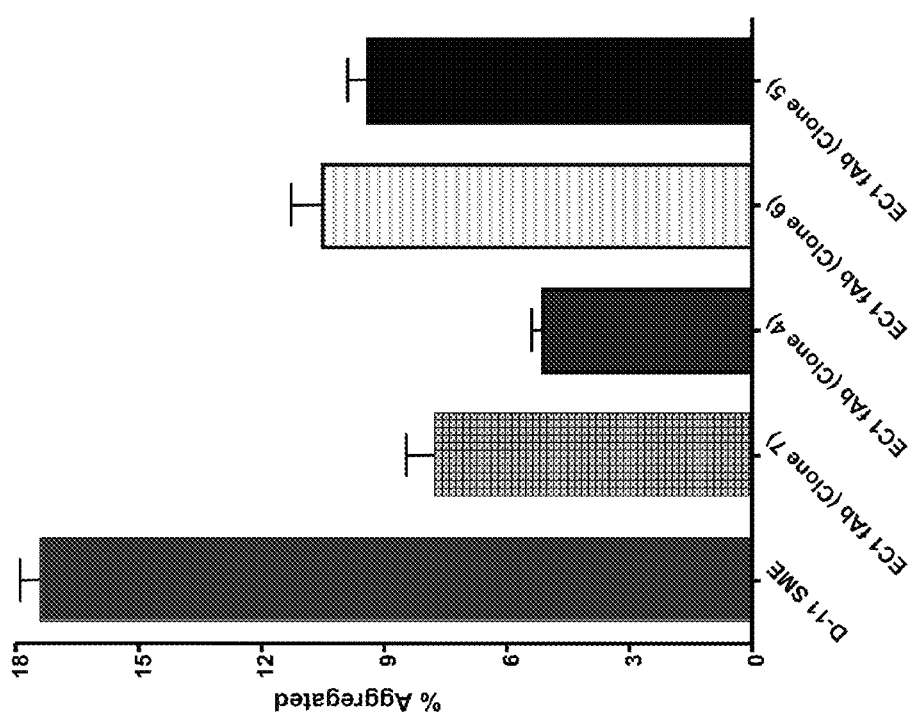

FIG. 6 is a graph depicting inhibition of Cad-11 mediated cell aggregation by various anti-Cadherin-11 EC1 Fabs that have binding specificity for Cad-11 alone (EC1 fAb clone 7 and clone 4), Cad-11 and Cad-8 (EC1 fAb clone 6), or Cad-11 and MN-Cad (EC1 fAb clone 5), using an in vitro cell aggregation assay. All Fabs tested inhibited 431-D-11 cell aggregation relative to the control (D-11 SME; left bar).

Figure 7:
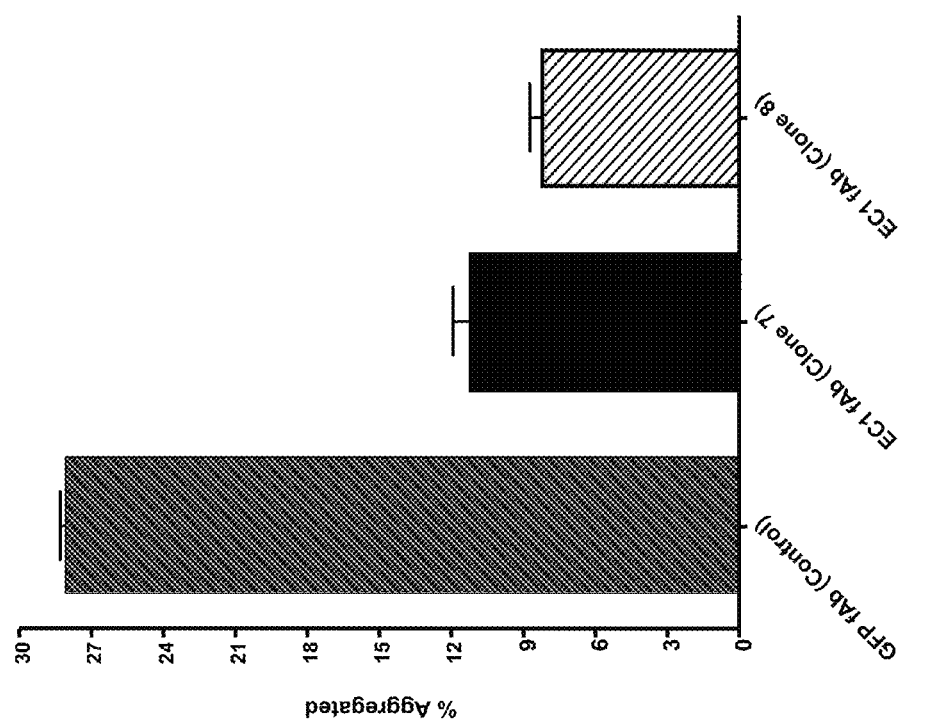

FIG. 7 is a graph depicting inhibition of Cad-11 mediated cell aggregation by anti-Cad-11 Fabs that have binding specificity for Cad-11 alone (EC1 fAb clone 7), or Cad-11 and MN-Cad (EC1 fAb clone 8), using an in vitro cell aggregation assay. The specificity of the Fabs tested is shown in parentheses next to each Fab designation. Both cadherin-specific Fabs inhibited cell aggregation (middle and right bars) relative to a control Fab that was specific for GFP (left bar).

FIG. 8 shows the nucleotide (DNA) sequence (SEQ ID NO:6) of the human Cad-11-EC1-hIgG2-Fc1 fusion protein (Cad-11-EC1-Fc). The sequence of the human Cadherin-11 extracellular domain is shown in italics, the BglII site is underlined, and the sequence encoding the human $IgG_2$-Fc1 region is shown in bold lettering.

FIG. 9 shows the amino acid sequence (SEQ ID NO:7) of the human Cad-11-EC1-hIgG2-Fc1 fusion protein (Cad-11-EC1-Fc). The sequence of the human Cadherin-11 extracellular domain is shown in italics, the sequence encoded by the BglII site is underlined, and the sequence of the human $IgG_2$-Fc1 region is shown in bold lettering.

Figure 10:
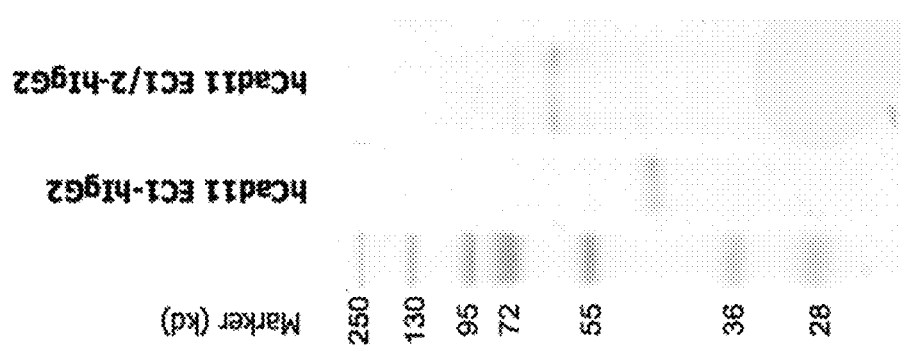

FIG. 10 is an image of an SDS polyacrylamide gel that has been stained with Coomassie Blue, which shows the predominant intense bands corresponding to the monomeric form of the purified Cad-11-EC1-$hIgG_2$-Fc1 (middle lane) and Cad-11-EC1/2-$hIgG_2$-Fc1 (right lane) fusion proteins, respectively, following purification from cell culture medium using a protein A column. Molecular weight standards are shown in the left lane.

Figure 11:
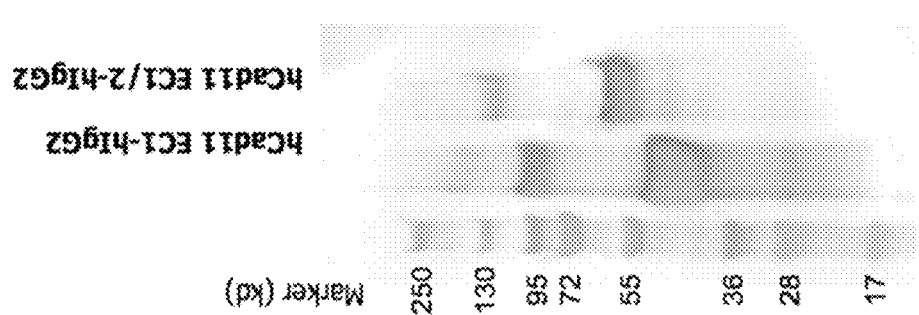

FIG. 11 is a Western blot showing the detection of human Cad-11-EC1-$hIgG_2$-Fc1 (middle lane) and Cad-11-EC1/2-$hIgG_2$-Fc1 (right lane) fusion proteins using an anti-human IgG antibody conjugated to horse radish peroxidase (HRP). The predominant observed band in each lane corresponds to the locations of the monomeric forms of the fusion proteins. The locations of the dimeric forms of the fusion proteins are also visible (see less intense higher molecular weight bands), due to incomplete reducing conditions. Molecular weight standards are shown in the left lane.

Figure 12:
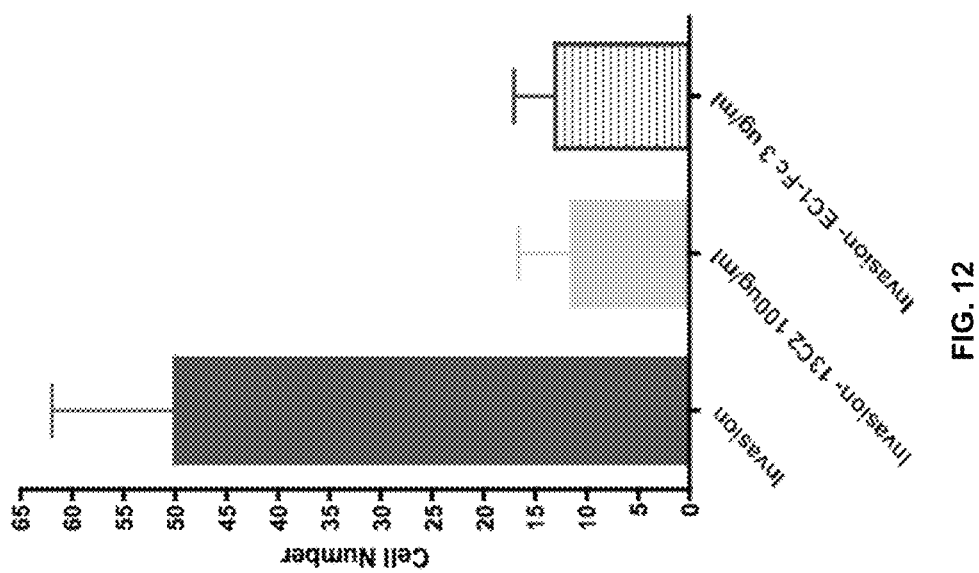

FIG. 12 is a graph depicting that a Cad-11-EC1-Fc fusion protein and a mouse anti-Cad-11 antibody, 13C2, inhibit the invasion of Cad-11 expressing human fibroblast-like synoviocytes into a matrigel plug at the indicated concentrations compared to untreated cells, labeled Invasion. Data is pooled from two independent experiments.

FIGS. 13A and B are graphs depicting data from two in vitro Cad-11 cell aggregation assays. Percent aggregation of Cad-11 expressing 431-D-11 cells is shown at 40 min. after addition of either SME media (designated control) or a Cad-11 fusion protein. FIG. 13A shows the inhibition of aggregation in the presence of varying concentrations of a fusion protein comprising the 5 extracellular domains of Cad-11 fused to the human IgG2 hinge, CH2 and CH3 domains (designated Cad-11-EC1-5-Fc). FIG. 13B shows the inhibition of aggregation of varying concentrations of a fusion protein comprising either the N-terminal extracellular domain (EC1 domain) of Cad-11 fused to the human IgG2 hinge, CH2 and CH3 domains (designated Cad-11-EC1-Fc) or Cad-11-EC1-5-Fc.

FIGS. 14A-C show the human Cadherin-11 cDNA sequence (SEQ ID NO:1; see Genbank Accession No. NM001797).

FIG. 15 shows the human Cadherin-11 protein sequence (SEQ ID NO:2; see Genbank Accession No. NP001788).

Figure 16:
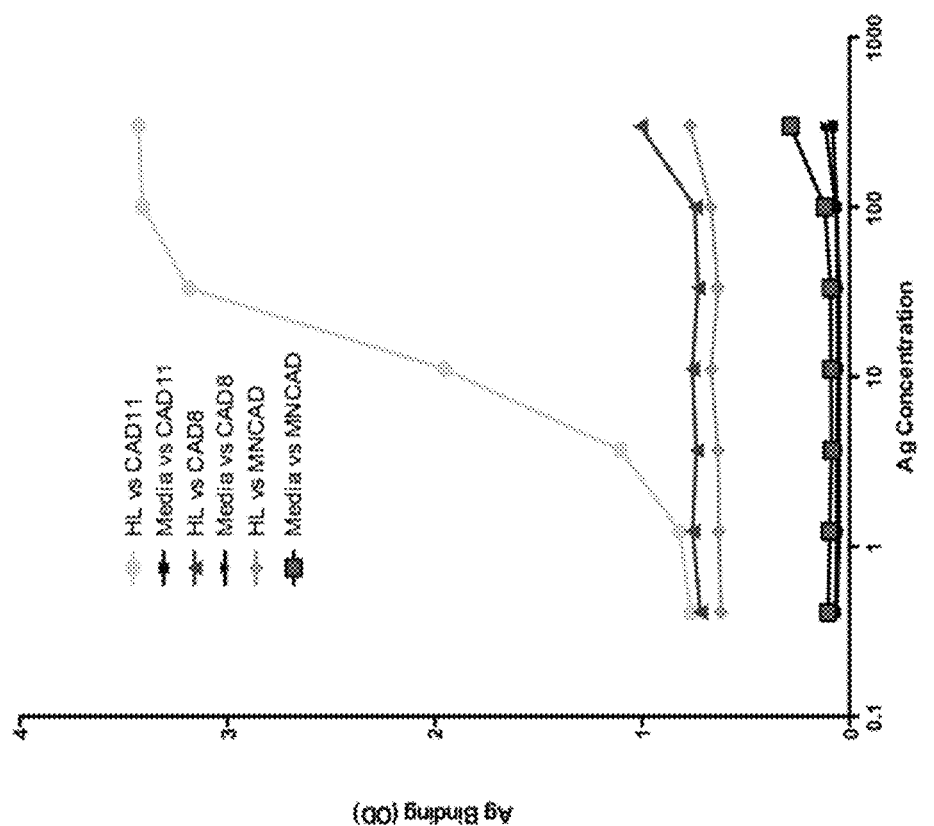

FIG. 16 is a graph depicting the level of binding of antibodies in media from peptide 4 hybridomas (HL), or control hybridoma media (Media), to proteins containing the EC1-2 domains of Cad-11, Cad-8 or MN-Cad, as determined by ELISA.

FIGS. 17A-C are representative graphs depicting the intensity of cell staining (MFI; mean fluorescence intensity) as a measure of binding of H14 antibody to Cad-11-expressing 431-D-11 cells.

FIGS. 17D-F are representative graphs depicting the absence of 431-D cell staining (MFI; mean fluorescence intensity) relative to FIGS. 17A-C, indicating a lack of binding of H14 antibody to the Cad-11 negative cells.

FIGS. 17G-I are representative graphs depicting the intensity of cell staining (MFI; mean fluorescence intensity) as a measure of binding of H1M1 antibody to Cad-11-expressing 431-D-11 cells.

Figures 18A, 18B:
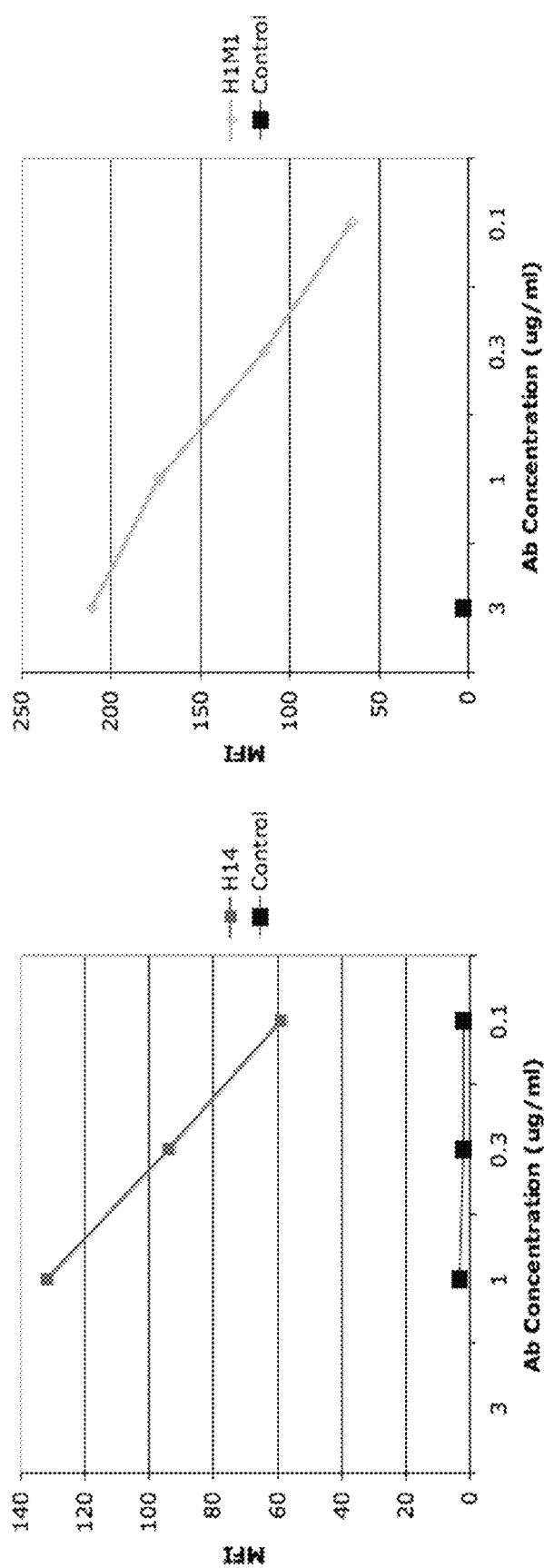

FIG. 18A is a graph depicting the binding of H14 antibody to Cad-11-expressing cells, and the absence of H14 binding to Cad-11 negative control cells, at varying concentrations of antibody, as measured by the intensity of cell staining (MFI; mean fluorescence intensity).

FIG. 18B is a graph depicting the binding of H1M1 antibody to Cad-11-expressing cells, and the absence of binding of H1M1 to Cad-11 negative control cells, at varying concentrations of antibody, as measured by the intensity of cell staining (MFI; mean fluorescence intensity).

FIG. 19A is a graph depicting the degree of binding of the H14 anti-Cad-11 antibody to Cad-11 and Cad-8 EC1 domain peptides at various antibody concentrations, as determined by ELISA.

FIG. 19B is a graph depicting the absence of binding of the H14 anti-Cad-11 antibody to Cad7, MNCad, Cad9, Cad18, Cad20 or Cad24 EC1 domain peptides at various antibody concentrations, as determined by ELISA.

Figure 20:
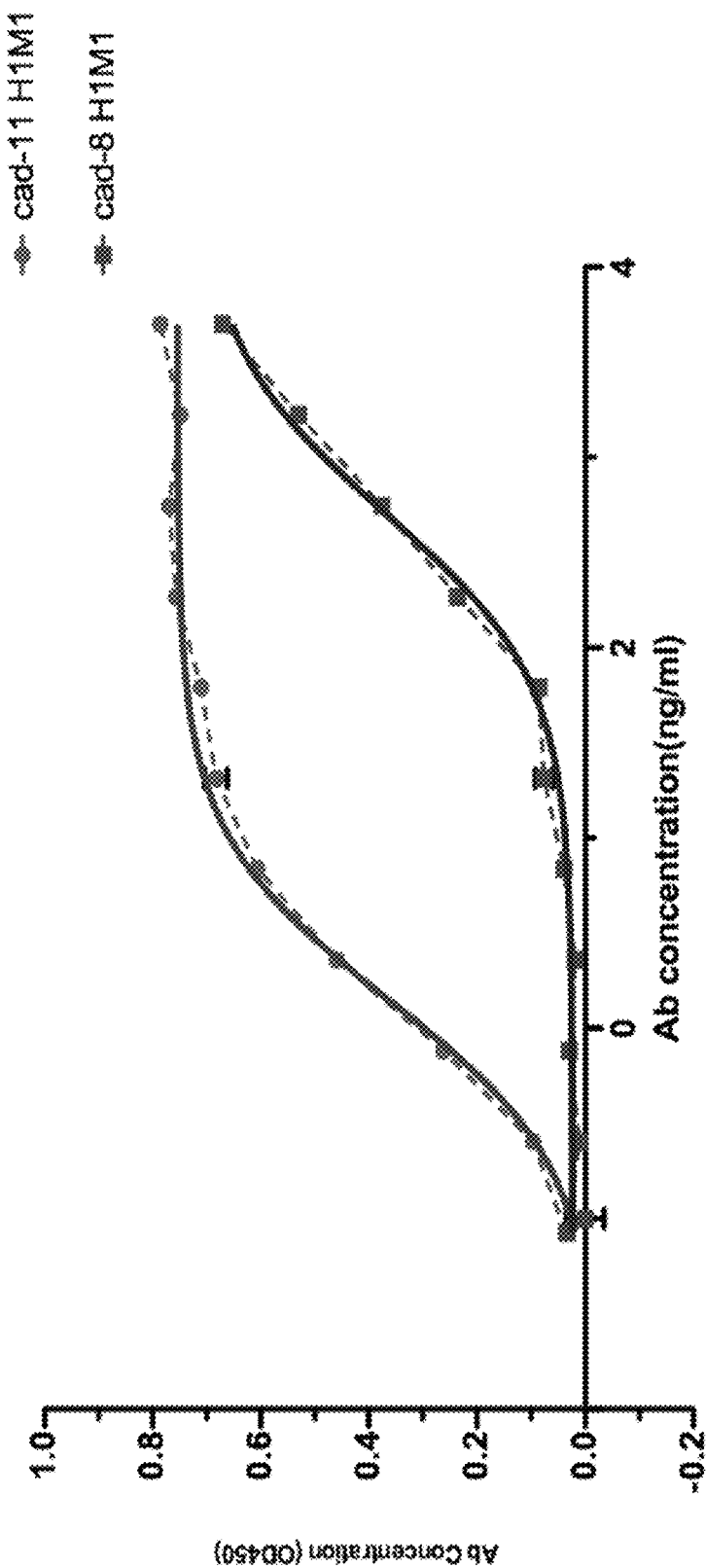

FIG. 20 is a graph depicting the binding of the H1M1 anti-Cad-11 antibody to Cad-11 and Cad-8 EC1 domain peptides at varying antibody concentrations, as determined by ELISA.

Figures 21A, 21B:
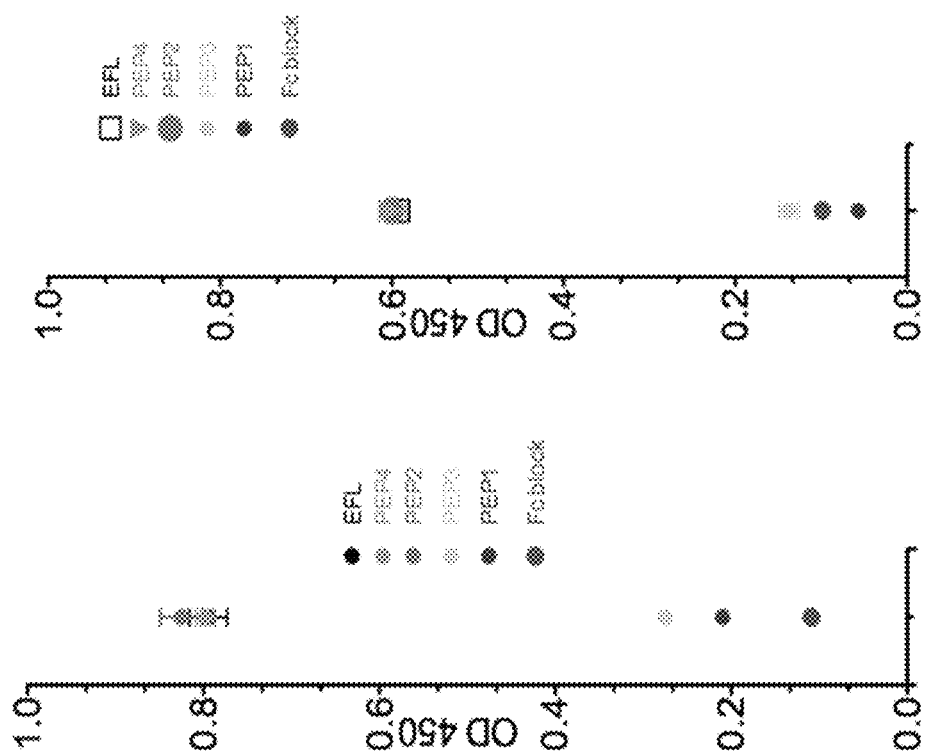

FIG. 21A is a graph depicting the degree of binding of the H1M1 anti-Cad-11 antibody to various Cad-11 EC1 domain peptide immunogens (PEP1, PEP2, PEP3 and PEP4), as well as the Cad-11 EC1 domain fusion protein (EFL) and human IgG control (Fc block), as determined by ELISA.

FIG. 21B is a graph depicting the degree of binding of the H14 anti-Cad-11 antibody to various Cad-11 EC1 domain peptide immunogens (PEP1, PEP2, PEP3 and PEP4), as well as the Cad-11 EC1 domain fusion protein (EFL) and human IgG control (Fc block), as determined by ELISA.

Figure 22:
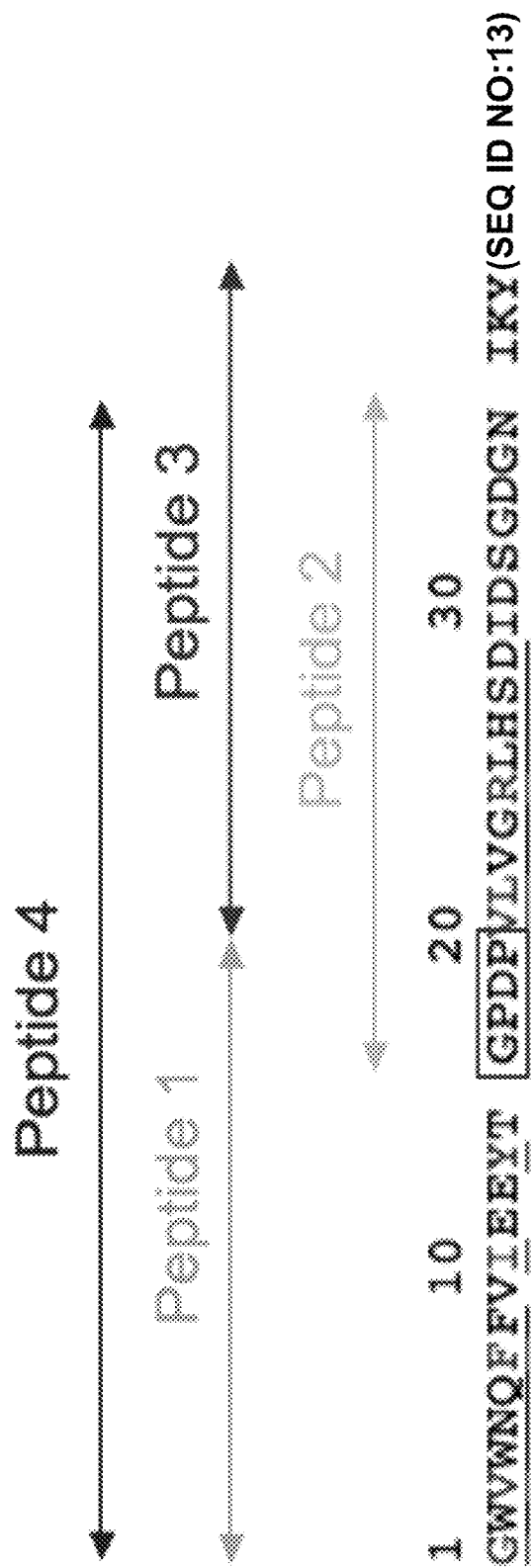

FIG. 22 is a schematic diagram depicting the sequence of the first 37 amino acids of the EC1 domain of human Cadherin-11 and the portions of this sequence encompassed by each of Peptides 1-4. Amino acid residues shared by Peptides 2 and 4 that are upstream of Peptide 3 are highlighted in the boxed region. Amino acids directly involved in Cad-11 to Cad-11 binding are underlined.

FIG. 23A is a photograph showing a large mass of aggregated Cad-11-expressing cells that were treated with a control isotype antibody.

FIG. 23B is a photograph showing small clumps of H1M1-treated Cad-11-expressing cells that did not progress to form the large masses observed in FIG. 23A.

FIG. 23C is a photograph showing that untreated parental Cad-11 negative cells remain as groups of single or double cells.

Figures 24A, 24B:
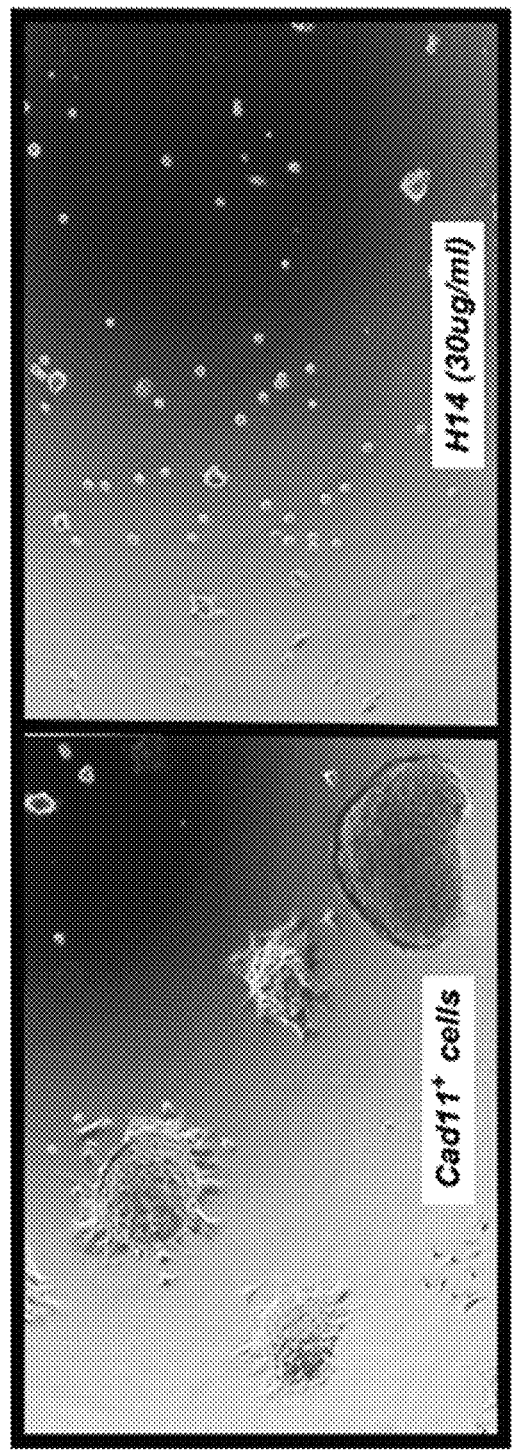

FIG. 24A is a photograph depicting a culture of Cad-11 expressing cells with large masses of aggregated cells.

FIG. 24B is a photograph depicting a culture of Cad-11 expressing cells with predominantly single cells with small and infrequent cell clusters relative to those shown in FIG. 24A following treatment with the H14 Cad-11 EC1 domain antibody.

Figure 25:
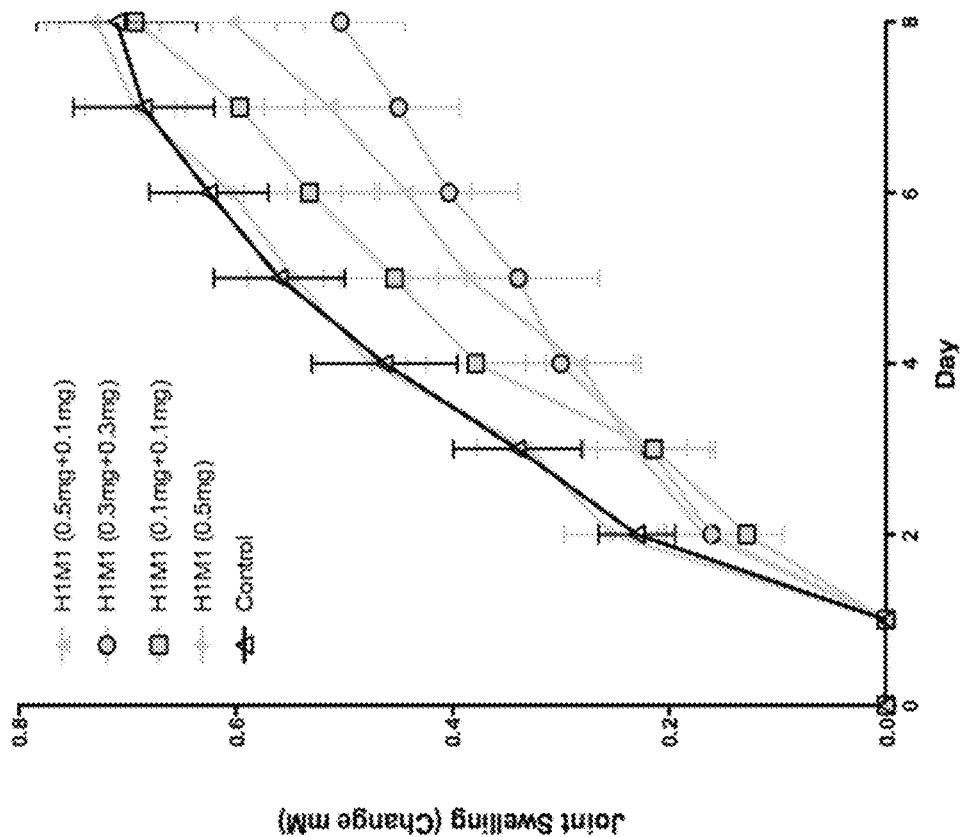

FIG. 25 is a graph depicting inhibition of arthritis-associated joint swelling in mice treated with increasing dosages of H1M1 anti-Cad-11 antibody relative to untreated control mice.

Figure 26:
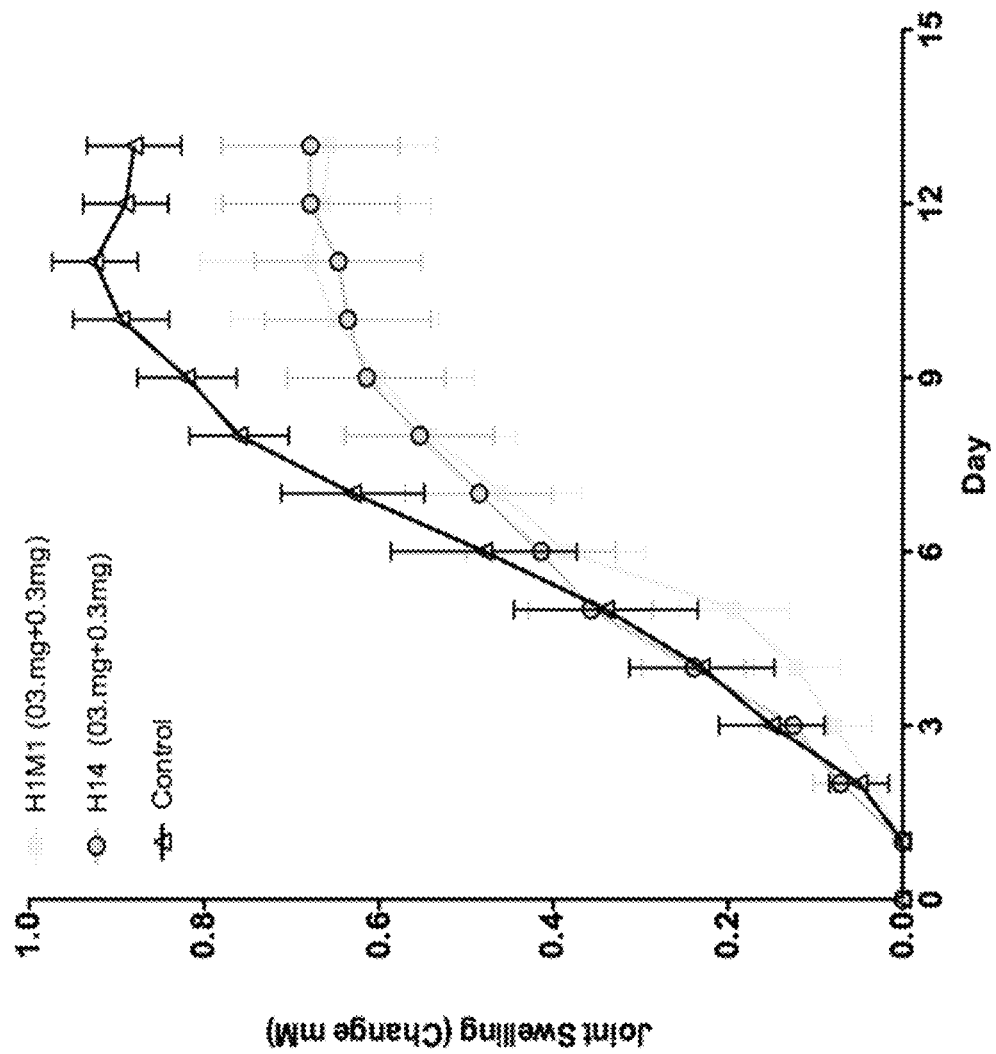

FIG. 26 is a graph depicting inhibition of arthritis-associated joint swelling in mice treated with 0.3 mg of either H14 or H1M1 anti-Cad-11 antibodies every second day relative to untreated control mice.

Figure 27:
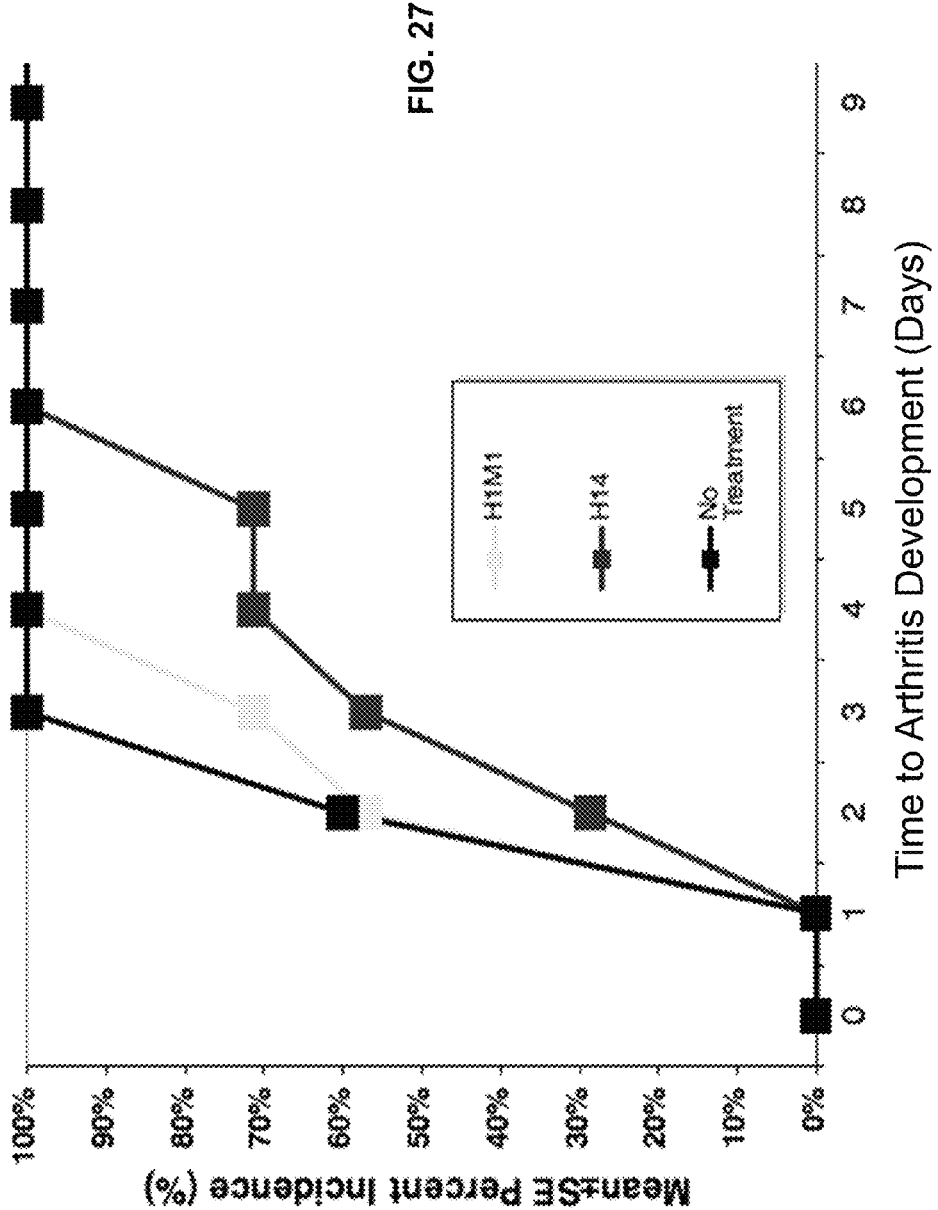

FIG. 27 is a graph showing that treatment with 0.3 mg of either H1M1 or H14 antibody delayed the development of arthritis in a mouse model compared to an untreated control.

Figure 28:
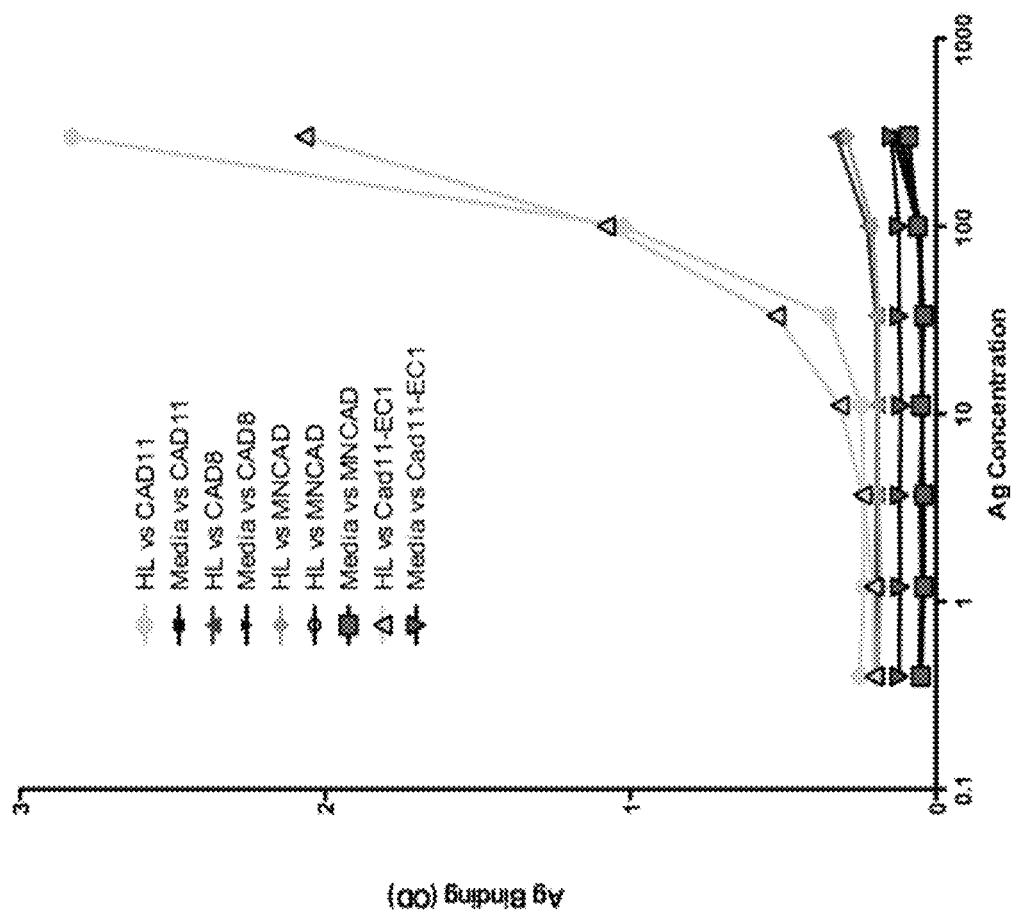

FIG. 28 is a graph depicting the degree of binding of antibody-containing media from peptide 3 hybridomas (HL), or control hybridoma media (Media), to the EC1-2 domains of Cad-11, Cad-8, and MN-Cadherin, or a Cad-11 EC1-Fc fusion protein.

Figure 29:
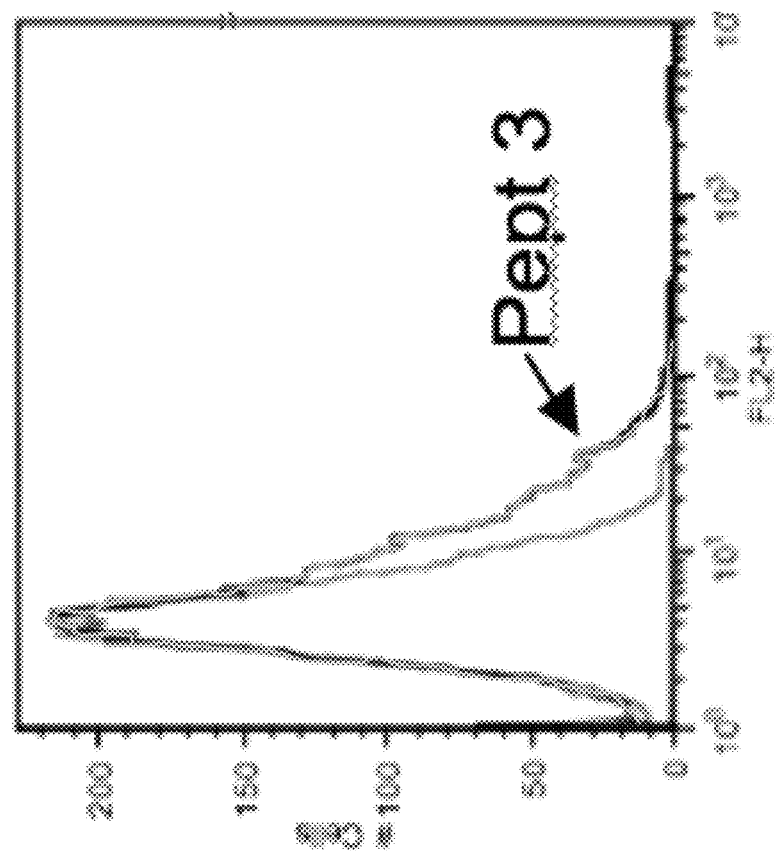

FIG. 29 is a graph depicting the degree of binding of anti-Cad-11 antibodies from the peptide 3 hybridomas to cells expressing human Cad-11 protein (see arrow) and non-Cad-11-expressing control cells that expressed Neos.

DETAILED DESCRIPTION OF THE INVENTION

Definitions

As used herein, the terms "Cadherin-11," "Cad-11," and "OB-Cadherin" refer to a naturally occurring or endogenous Cadherin-11 (e.g., mammalian, for example human) protein, and to proteins having an amino acid sequence that is the same as that of naturally occurring or endogenous Cadherin-11 protein (e.g., recombinant proteins, synthetic proteins). Accordingly, the terms "Cadherin-11," "Cad-11," and "OB-Cadherin," which are used interchangeably herein, include polymorphic or allelic variants and other isoforms of a Cadherin-11 protein (e.g., mammalian, human) produced by, e.g., alternative splicing or other cellular processes, that occur naturally in mammals (e.g., humans, non-human primates). Preferably, the Cadherin-11 protein is a human protein that has the amino acid sequence of SEQ ID NO:2 (See, Genbank Accession No. NP001788 and FIG. 15).

As defined herein, a "Cadherin-11 antagonist" is an agent (e.g., antibody, fusion protein, peptide, peptidomimetic, small molecule, nucleic acid) that specifically binds an EC1 domain of a Cadherin-11 protein and inhibits (e.g., reduces, prevents) one or more Cadherin-11-mediated activities in a cell. Cadherin-11-mediated activities include, but are not limited to, binding of a Cadherin-11 protein to one or more other Cadherin-11 proteins in a homotypic fashion, aggregation of cells that express Cadherin-11, induction of enzyme (e.g., collagenase, serine proteases, MMP1, MMP3, MMP13) expression or activity, and induction of cytokines or growth factors (e.g., IL-6, IL-8 or RANKL or TRANCE). In one embodiment, the Cadherin-11 antagonist can inhibit the binding of a Cadherin-11 protein to one or more other Cadherin-11 proteins by, for example, blocking the interaction between the donor sequences in the EC1 domain of a Cad-11 protein (e.g., a Cad-11 protein expressed on the surface of a cell) with the pocket sequence in the EC1 domain of one or more other Cad-11 proteins (e.g., one or more Cad-11 proteins expressed on the surface of another cell).

As used herein, a Cadherin-11 antagonist that "specifically binds" an EC1 domain of a Cadherin-11 protein refers to a Cadherin-11 antagonist that binds (e.g., under physiological conditions) an EC1 domain of a Cadherin-11 protein with an affinity (e.g., a binding affinity) that is at least about 5 fold, preferably at least about 10 fold, greater than the affinity with which the Cadherin-11 antagonist binds an EC1 domain of another cadherin protein (e.g., MN-Cadherin, Cadherin-8). In a particular embodiment, the Cadherin-11 antagonist that specifically binds an EC1 domain of a Cadherin-11 protein binds an epitope present in SEQ ID NO:3, the N-terminal portion of the EC1 domain of human Cadherin-11, with an affinity that is at least about 5 fold, preferably at least about 10 fold, greater than the affinity with which the Cadherin-11 antagonist binds an epitope present in SEQ ID NO:4, the N-terminal portion of the EC1 domain of human MN-Cadherin, and the affinity with which the Cadherin-11 antagonist binds an epitope present in SEQ ID NO:5, the N-terminal portion of the EC1 domain of human Cadherin-8.

As used herein, the term "antibody" is intended to encompass both whole antibodies and antibody fragments (e.g., antigen-binding fragments of antibodies, for example, Fv, Fc, Fd, Fab, Fab', F(ab'), and dAb fragments). "Antibody" refers to both polyclonal and monoclonal antibodies and includes naturally-occurring and engineered antibodies. Thus, the term "antibody" includes, for example, human, chimeric, humanized, primatized, veneered, single chain, and domain antibodies (dAbs). (See e.g., Harlow et al., *Antibodies A Laboratory Manual*, Cold Spring Harbor Laboratory, 1988).

The term "epitope" refers to a unit of structure conventionally bound by an immunoglobulin $V_H/V_L$ pair. An epitope defines the minimum binding site for an antibody, and thus represent the target of specificity of an antibody.

The term "fusion protein" refers to a naturally occurring, synthetic, semi-synthetic or recombinant single protein molecule that comprises all or a portion of two or more heterologous polypeptides.

The term "polypeptide" refers to a polymer of amino acids, and not to a specific length; thus, peptides, oligopeptides and proteins are included within the definition of a polypeptide.

As used herein, the term "peptide" refers to a compound consisting of from about 2 to about 100 amino acid residues wherein the amino group of one amino acid is linked to the carboxyl group of another amino acid by a peptide bond. Such peptides are typically less than about 100 amino acid residues in length and preferably are about 10, about 20, about 30, about 40 or about 50 residues.

As used herein, the term "peptidomimetic" refers to molecules which are not peptides or proteins, but which mimic aspects of their structures. Peptidomimetic antagonists can be prepared by conventional chemical methods (see e.g., Damewood J. R. "Peptide Mimetic Design with the Aid of Computational Chemistry" in *Reviews in Computational Biology*, 2007, Vol. 9, pp. 1-80, John Wiley and Sons, Inc., New York, 1996; Kazmierski W. K., "*Methods of Molecular Medicine: Peptidomimetic Protocols*," Humana Press, New Jersey, 1999).

As defined herein, "therapy" is the administration of a particular therapeutic or prophalytic agent to a subject (e.g., a mammal, a human), which results in a desired therapeutic or prophylactic benefit to the subject.

As defined herein a "treatment regimen" is a regimen in which one or more therapeutic or prophalytic agents are administered to a mammalian subject at a particular dose (e.g., level, amount, quantity) and on a particular schedule or at particular intervals (e.g., minutes, days, weeks, months).

As defined herein, a "therapeutically effective amount" is an amount sufficient to achieve the desired therapeutic or prophylactic effect under the conditions of administration, such as an amount sufficient to inhibit (i.e., reduce, prevent) inflammation in a joint (e.g., by inhibiting the aggregation of cells, for example synoviocytes, that express Cadherin-11). The effectiveness of a therapy (e.g., the reduction of inflammation in a joint and/or prevention of inflammation in a joint) can be determined by suitable methods (e.g., imaging methods, such as MRI, NMR, CT).

Cadherins

Cadherins belong to a large family of $Ca^{2+}$-dependent adhesion molecules that mediate cell adhesion by binding to other cadherins in a homotypic manner (M J Wheelock and K R Johnson, *Ann. Rev. Cell Dev. Biol.* 19: 207-235 (2003). Classical cadherins are single-pass transmembrane proteins that contain five extracellular cadherin (EC) domains, each approximately 110 amino acids in length, a transmembrane region and a conserved cytoplasmic domain. Cadherins are divided into either type I or type II cadherins based on the degree of homology between the EC domains. Type II cadherins include human cadherins-5, -6, -8, -11, and -12, and MN-cadherin. The relative importance of the role of each of the extracellular domains in mediating inter-cellular binding is unclear.

Cadherin-11 Activity in Synoviocytes

Cadherin-11 mediates synoviocyte to synoviocyte binding in the synovial lining of articulated joints (Valencia et al., *J. Exp. Med.* 200(12):1673-1679 (2004); Kiener and Brenner, *Arthritis Res Ther.* 7(2):49-54 (2005)). A fusion protein that comprised all five extracellular cadherin domains of human Cadherin-11, fused to the hinge-CH2-CH3 domain of human $IgG_2$, inhibited synoviocyte lining formation in vitro (Kiener et al., *Am. J. Pathol.* 168 (2006)). In addition, antagonistic anti-Cadherin-11 antibodies and a fusion protein that comprised EC1-5 of murine Cadherin-11, fused to the hinge-$CH_2$—$CH_3$ domains of murine IgG2a, inhibited inflammation and joint swelling in murine models of rheumatoid arthritis (Lee et al., *Science* 315:1006-1010 (2007)).

Cadherin-11 Antagonists

A Cadherin-11 antagonist of the invention can be any agent that specifically binds an EC1 domain of a Cadherin-11 protein and inhibits (e.g., reduces, prevents) one or more Cadherin-11-mediated activities in a cell. Cadherin-11-mediated activities include, but are not limited to, aggregation of cells that express Cadherin-11 on the cell surface, and expression or secretion of factors such as, for example, collagenase, serine proteases, MMP1, MMP3, IL-6, IL-8 or RANKL/TRANCE. The agent can be an antibody, a fusion protein, a peptide, a peptidomimetic, a small molecule, or a nucleic acid, among others.

Cadherin-11 Antibodies

As described herein, antibodies that bind an epitope within an N-terminal portion of the EC1 domain of human Cadherin-11 that comprises the donor sequences and cadherin-binding pocket of Cad-11 (e.g., SEQ ID NO:3), block Cadherin-11 activity in vitro more effectively than antibodies that bind to epitopes in other regions of this protein (See Examples 1 and 2).

Accordingly, in one embodiment, the invention provides an antibody or antigen-binding fragment thereof that binds (e.g., specifically binds) an epitope that is present in the N-terminal portion of the EC1 domain of a Cadherin-11 protein that comprises the donor sequences and cadherin-binding pocket of Cad-11. The term "antibody" is intended to encompass all types of polyclonal and monoclonal antibodies (e.g., human, chimeric, humanized, primatized, veneered, single chain, domain antibodies (dAbs)) and antigen-binding fragments of antibodies (e.g., Fv, Fc, Fd, Fab, Fab', F(ab'), dAb). (See e.g., Harlow et al., *Antibodies A Laboratory Manual*, Cold Spring Harbor Laboratory, 1988). In a particular embodiment, the Cad-11 EC1 domain-specific antibody is a human antibody or humanized antibody. Cad-11 EC1 domain-specific antibodies can also be directly or indirectly linked to a cytotoxic agent.

Other antibodies or antibody fragments that specifically bind to an N-terminal portion of the EC1 domain of a Cad-11 protein and inhibit the activity of the Cad-11 protein can also be produced, constructed, engineered and/or isolated by conventional methods or other suitable techniques. For example, antibodies which are specific for the EC1 domain of a Cadherin-11 protein can be raised against an appropriate immunogen, such as a recombinant mammalian (e.g., human) Cadherin-11 EC1 domain peptide (e.g., SEQ ID NO:3) or a portion thereof (including synthetic molecules, e.g., synthetic peptides). A variety of methods have been described (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Antibodies can also be raised by immunizing a suitable host (e.g., mouse) with cells that express the EC1 domain of Cadherin-11 (e.g., cancer cells/cell lines) or cells engineered to express the EC1 domain of Cadherin-11 (e.g., transfected cells). (See e.g., Chuntharapai et al., *J. Immunol.*, 152:1783-1789 (1994); Chuntharapai et al. U.S. Pat. No. 5,440,021). For the production of monoclonal antibodies, a hybridoma can be produced by fusing a suitable immortal cell line (e.g., a myeloma cell line such as SP2/0 or P3X63Ag8.653) with antibody producing cells. The antibody producing cells can be obtained from the peripheral blood, or preferably, the spleen or lymph nodes, of humans or other suitable animals immunized with the antigen of interest. The fused cells (hybridomas) can be isolated using selective culture conditions, and cloned by limited dilution. Cells which produce antibodies with the desired specificity can be selected by a suitable assay (e.g., ELISA).

Antibody fragments can be produced by enzymatic cleavage or by recombinant techniques. For example, papain or pepsin cleavage can generate Fab or $F(ab')_2$ fragments, respectively. Other proteases with the requisite substrate specificity can also be used to generate Fab or $F(ab')_2$ fragments. Antibodies can also be produced in a variety of truncated forms using antibody genes in which one or more stop codons has been introduced upstream of the natural stop site. For example, a chimeric gene encoding a $F(ab')_2$ heavy chain portion can be designed to include DNA sequences encoding the $CH_1$ domain and hinge region of the heavy chain. Single chain antibodies, and human, chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194, 276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science,* 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.,* 17: 5404 (1989)); Sato, K., et al., *Cancer Research,* 53: 851-856 (1993); Daugherty, B. L. et al., *Nucleic Acids Res.,* 19(9): 2471-2476 (1991); and Lewis, A. P. and J. S. Crowe, *Gene,* 101: 297-302 (1991)). Using these or other suitable methods, variants can also be readily produced. In one embodiment, cloned variable regions (e.g., dAbs) can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see e.g., Jakobovits et al., *Proc. Natl. Acad. Sci. USA,* 90: 2551-2555 (1993); Jakobovits et al., *Nature*, 362: 255-258 (1993); Lonberg et al., U.S. Pat. No. 5,545,806; Surani et al., U.S. Pat. No. 5,545,807; Lonberg et al., WO 97/13852).

The invention encompasses, in one embodiment, a Cad-11 antibody that binds to an epitope that is present in the first about 37 amino acids of the EC1 domain of human Cad-11 (SEQ ID NO: 13). In a particular embodiment, the invention relates to a Cad-11 antibody that binds to an epitope that is present in SEQ ID NO:10. In a further embodiment, the invention relates to a Cad-11 antibody that binds to an epitope that comprises SEQ ID NO:11. In another embodiment, the invention relates to a Cad-11 antibody that binds to an epitope that is present in SEQ ID NO:12.

In one embodiment, the invention relates to a Cad-11 antibody produced by hybridoma H1M1 (ATCC accession number PTA-9699), having been deposited on Jan. 8, 2009 at the American Type Culture Collection (ATCC), 10801 University Boulevard, Manassas, Va. 20110, United States of America. In another embodiment, the invention provides a Cad-11 antibody produced by hybridoma H14 (ATCC accession number PTA-9701), having been deposited on Jan. 8, 2009 at the American Type Culture Collection (ATCC), 10801 University Boulevard, Manassas, Va. 20110, United States of America.

The invention also encompasses antibodies that specifically compete with a Cad-11 antibody produced by hybridoma H1M1 and/or a Cad-11 antibody produced by hybridoma H14 for binding to a human Cad-11 protein or an EC1-domain containing portion thereof (e.g., SEQ ID NO:3, 10, 12, 13). In a particular embodiment, an antibody that specifically competes with a Cad-11 antibody produced by hybridoma H1M1 and/or hybridoma H14 blocks (e.g., inhibits, diminishes, prevents) the binding of a Cad-11 antibody produced by hybridoma H1M1 and/or hybridoma H14 to a human Cad-11 protein or EC1-domain containing portion thereof (e.g., SEQ ID NO:3, 10, 12, 13).

In addition, the invention encompasses antibodies having a binding affinity for a human Cad-11 protein or EC1-domain containing portion thereof (e.g., SEQ ID NO:3, 10, 12, 13) that is at least as great as the binding affinity of a Cad-11 antibody produced by hybridoma H1M1 and/or a Cad-11 antibody produced by hybridoma H14 for a human Cad-11 protein or EC1-domain containing portion thereof.

Cadherin-11 Fusion Proteins

In addition, immunoglobulin fusion proteins that contain only the EC1 domain of human Cad-11 (e.g., the EC1 domain of human Cad-11 fused to a portion of human IgG) inhibited Cad-11 activity in vitro more effectively than a fusion protein that included a larger portion of the EC region of Cad-11, which contained all 5 EC domains.

Cadherin-11 antagonists also encompass chimeric, or fusion, proteins that comprise at least about the N-terminal 35 amino acids of the EC1 domain of human Cad-11 (SEQ ID NO:2) operatively linked to all or a portion of a heterologous protein. "Operatively linked" indicates that the portion of the Cad-11 EC1 domain and the heterologous protein are fused in-frame. The heterologous protein can be fused to the N-terminus or C-terminus of the protein. For example, the fusion protein can be a GST-fusion protein in which the protein sequences are fused to the C-terminus of a GST sequence. Other types of fusion proteins include, but are not limited to, enzymatic fusion proteins, for example, β-galactosidase fusion proteins, yeast two-hybrid GAL fusion proteins, poly-His fusions, FLAG-tagged fusion proteins, GFP fusion proteins, and immunoglobulin (Ig) fusion proteins. Such fusion protein can facilitate purification (e.g., of a recombinant fusion protein). In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (see, for example, EP-A 0232 262). In drug discovery, for example, human proteins have been fused with Fc portions for the purpose of high-throughput screening assays to identify antagonists (Bennett et al., *Journal of Molecular Recognition* 8:52-58 (1995); Johanson et al., *J. Biol. Chem.,* 270(16): 9459-9471 (1995)). Thus, this invention also encompasses soluble fusion proteins containing a protein Cad-11 antagonist of the invention and various portions of the constant regions of heavy and/or light chains of immunoglobulins of various subclasses (e.g., IgG, IgM, IgA, IgE). Advantages of immunoglobulin fusion proteins of the present invention include one or more of the following: (1) increased avidity for multivalent ligands due to the resulting bivalency of dimeric fusion proteins, (2) longer serum half-life, (3) the ability to activate effector cells via the Fc domain, (4) ease of purification (for example, by protein A chromatography), (5) affinity for Cad-11 and (6) the ability to block Cad-11 mediated activity.

Accordingly, in particular embodiments, the Cad-11 antagonist is a fusion protein that comprises a portion of the extracellular region of a Cadherin-11 protein that includes an N-terminal portion of the EC1 domain (amino acids 54-90 of SEQ ID NO:2), operatively linked to all, or a portion of, a mammalian immunoglobulin protein. In a particular embodiment, the immunoglobulin fusion proteins of the invention do not comprise a portion of the extracellular region of Cadherin-11 that includes all five EC domains that are contained within amino acids 1-609 of SEQ ID NO:2. In certain embodiments, the portion of the human Cadherin-11 extracellular region can include, for example, amino acids 1-160, amino acids 1-259 or amino acids 1-269 of SEQ ID NO:2. In a particular embodiment, the fusion protein lacks the leader and pro-region of human Cadherin-11 (amino acids 1-53 of SEQ ID NO:2) and uses a heterogologous leader sequence. The immunoglobulin portion can be from any vertebrate source, such as murine, but preferably, is a human immunoglobulin protein. In one embodiment, the mammalian immunoglobulin protein is a human $IgG_2$ protein or a portion thereof, such as the hinge-$CH_2$—$CH_3$ portion of human $IgG_2$.

A chimeric or fusion protein of the invention can be produced by standard recombinant DNA techniques. For example, DNA fragments coding for different protein sequences (e.g., a Cad-11 EC1 domain peptide and a mammalian immunoglobulin) are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992). Moreover, many expression vectors are commercially available that already encode a fusion moiety (e.g., a GST moiety, an Fc moiety). A nucleic acid molecule encoding protein Cad-11 antagonist can be cloned into such an expression vector that the fusion moiety (e.g., immunoglobulin) is linked in-frame to the protein.

The immunoglobulin fusion proteins of the invention can be provided as monomers, dimers, tetramers or other multimers (e.g., polymers). For example, variable domains of the immunoglobulin portion of the fusion protein may be linked together to form multivalent ligands by, for example, provision of a hinge region at the C-terminus of each V domain and disulphide bonding between cysteines in the hinge regions; or provision of heavy chains each with a cysteine at the C-terminus of the domain, the cysteines being disulphide bonded together; or production of V-CH & V-CL to produce a Fab format; or use of peptide linkers (for example $Gly_4Ser$ linkers) to produce dimers, trimers and further multimers. For example, such ligands can be linked to an antibody Fc region comprising one or both of $C_H2$ and $C_H3$ domains, and optionally a hinge region. For example, vectors encoding ligands linked as a single nucleotide sequence to an Fc region may be used to prepare such ligands (e.g., by expression).

The immunoglobulin fusion proteins of the invention can be conjugated to other moieties including, but not limited to, multimers of polyethelene glycol (PEG) or its derivatives (e.g., poly methyl ethylene glycol), radionuclides, cytotoxic agents and drugs, and subsequently used for in vivo therapy. Examples of radionuclides include $^{212}Bi$, $^{131}I$, $^{186}Re$, and $^{90}Y$, among others. The radionuclides exert their cytotoxic effect by locally irradiating the cells, leading to various intracellular lesions, as is known in the art of radiotherapy. Cytotoxic drugs that can be conjugated to the fusion proteins include, but are not limited to, daunorubicin, doxorubicin, methotrexate, and Mitomycin C. Cytotoxic drugs interfere with critical cellular processes including DNA, RNA, and protein synthesis. For a fuller exposition of these classes of drugs, which are known in the art, and their mechanisms of action, see Goodman, A. G., et al., *Goodman and Gilman's The Pharmacological Basis of Therapeutics*, 8th Ed., Macmillan Publishing Col, 1990. Katzung, ed., Basic and Clinical Pharmacology, Fifth Edition, p 768-769, 808-809, 896, Appleton and Lange, Norwalk, Conn.

As used herein, the term "immunoglobulin fusion protein" includes fragments of the immunoglobulin fusion proteins of the invention. Such fragments are intended to be within the scope of this invention. For example, once the molecules are isolated, they can be cleaved with protease to generate fragments that remain capable of binding the EC1 domain of human Cad-11.

Peptide Antagonists

The Cadherin-11 antagonist of the invention can also be a peptide that binds to the EC1 domain of a Cadherin-11 protein. The peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*", John Wiley and Sons, 1991. The functional groups of a peptide can also be derivatized (e.g., alkylated) using art-known methods.

The peptide Cad-11 antagonist can comprise one or more modifications (e.g., amino acid linkers, acylation, acetylation, amidation, methylation, terminal modifiers (e.g., cyclizing modifications)), if desired. The peptide can also contain chemical modifications (e.g., N-methyl-α-amino group substitution). In addition, the peptide antagonist can be an analog of a known and/or naturally-occurring peptide, for example, a peptide analog having conservative amino acid residue substitution(s). These modifications can improve various properties of the peptide (e.g., solubility, binding), including its Cadherin-11 antagonist activity.

Cad-11 antagonists that are peptides can be linear, branched or cyclic, e.g., a peptide having a heteroatom ring structure that includes several amide bonds. In a particular embodiment, the peptide is a cyclic peptide. Such peptides can be produced by one of skill in the art using standard techniques. For example, a peptide can be derived or removed from a native protein by enzymatic or chemical cleavage, or can be synthesized by suitable methods, for example, solid phase peptide synthesis (e.g., Merrifield-type synthesis) (see, e.g., Bodanszky et al. "*Peptide Synthesis*," John Wiley & Sons, Second Edition, 1976). Peptides that are Cadherin-11 antagonists can also be produced, for example, using recombinant DNA methodologies or other suitable methods (see, e.g., Sambrook J. and Russell D. W., *Molecular Cloning: A Laboratory Manual*, 3$^{rd}$ Edition, Cold Spring Harbor Laboratory Press, Cold Spring Harbor, N.Y., 2001).

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide antagonists can then be isolated using suitable methods.

Peptidomimetic Antagonists

Cadherin-11 antagonists can also be peptidomimetics. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with amino acids in the EC1 domain of Cad-11. For example, the binding moieties in a peptidomimetic can be the same as those in a peptide or protein antagonist. The binding moieties can be an atom or chemical group which reacts with the receptor in the same or similar manner as the binding moiety in the peptide antagonist. For example, computational chemistry can be used to design peptide mimetics of the donor sequences of the EC1 domain of a Cadherin-11 protein, for instance, which can bind to the pocket sequence in the EC1 domain of Cad-11 proteins. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more-CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

Small Molecule Antagonists

Cadherin-11 antagonists can also be small molecules. Examples of small molecules include organic compounds, organometallic compounds, inorganic compounds, and salts of organic, organometallic or inorganic compounds. Atoms in a small molecule are typically linked together via covalent and/or ionic bonds. The arrangement of atoms in a small organic molecule may represent a chain (e.g. a carbon-carbon chain or a carbon-heteroatom chain), or may represent a ring containing carbon atoms, e.g. benzene or a polycyclic system, or a combination of carbon and heteroatoms, i.e., heterocycles such as a pyrimidine or quinazoline. Although small molecules can have any molecular weight, they generally include molecules that are less than about 5,000 daltons. For example, such small molecules can be less than about 1000 daltons and, preferably, are less than about 750 daltons or, more preferably, are less than about 500 daltons. Small molecules and other non-peptidic Cadherin-11 antagonists can be found in nature (e.g., identified, isolated, purified) and/or produced synthetically (e.g., by traditional organic synthesis, bio-mediated synthesis, or a combination thereof). See e.g. Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

A small molecule Cadherin-11 antagonist according to the present invention, and physiologically acceptable salts thereof, can inhibit the homotypic binding of a Cadherin-11 protein (e.g., by directly competing with a donor sequence in the EC1 domain of a Cad-11 protein for binding to the binding pocket of another Cadherin-11, by directly competing with the binding pocket in the EC1 domain of a Cad-11 protein for binding to a donor sequence of another Cadherin-11).

Nucleic Acid Antagonists

Cad-11 antagonists of the invention can also be nucleic acid molecules (e.g., oligonucleotides) that bind to the EC1 domain of a human Cadherin-11. Suitable nucleic acid Cad-11 antagonists include aptamers, which are capable of binding to a particular molecule of interest (e.g., the EC1 domain of human Cadherin-11) with high affinity and specificity through interactions other than classic Watson-Crick base pairing (Tuerk and Gold, Science 249:505 (1990); Ellington and Szostak, Nature 346:818 (1990)).

Aptamers, like peptides generated by phage display or monoclonal antibodies (MAbs), are capable of specifically binding to selected targets and, through binding, block their targets' ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

An aptamer that binds to a target of interest (e.g., an EC1 domain of a human Cad-11 protein) can be generated and identified using a standard process known as "Systematic Evolution of Ligands by Exponential Enrichment" (SELEX), described in, e.g., U.S. Pat. No. 5,475,096 and U.S. Pat. No. 5,270,163.

Identification of Cadherin-11 Antagonists

Agents having Cadherin-11 binding specificity, including small molecules, can be identified in a screen, for example, a high-throughput screen of chemical compounds and/or libraries (e.g., chemical, peptide, nucleic acid libraries).

Antibodies that specifically bind the EC1 domain of human Cadherin-11 can be identified, for example, by screening commercially available combinatorial antibody libraries (Dyax Corp., MorphoSys AG). Suitable combinatorial antibody libraries and standard methods of screening these libraries are described in Hoet et al., *Nature Biotechnology* 23(3): 344-348 (2005) and Rauchenberger et al., *J. Biol. Chem.* 278(40):38194-38205 (2003), the contents of which are incorporated herein by reference. Such libraries or collections of molecules can also be prepared using well-known chemical methods.

Alternatively murine antibodies that specifically bind the EC1 domain of human Cadherin-11 can be identified, for example, by immunizing mice with EC1 protein domains or EC1 peptides along with an adjuvant to break tolerance to the antigen. These antibodies can be screened for the desired specificity and activity and then humanized using known techniques to create suitable agents for the treatment of human disease.

Compounds or small molecules can be identified from numerous available libraries of chemical compounds from, for example, the Chemical Repository of the National Cancer Institute and the Molecular Libraries Small Molecules Repository (PubChem), as well as libraries of the Institute of Chemistry and Cell Biology at Harvard University and other libraries that are available from commercial sources (e.g., Chembridge, Peakdale, CEREP, MayBridge, Bionet). Such libraries or collections of molecules can also be prepared using well-known chemical methods, such as well-known methods of combinatorial chemistry. The libraries can be screened to identify compounds that bind and inhibit Cadherin-11.

Identified compounds can serve as lead compounds for further diversification using well-known methods of medicinal chemistry. For example, a collection of compounds that are structural variants of the lead can be prepared and screened for Cadherin-11 binding and/or inhibitory activity. This can result in the development of a structure activity relationship that links the structure of the compounds to biological activity. Compounds that have suitable binding and inhibitory activity can be developed further for in vivo use.

Agents that bind Cadherin-11 can be evaluated further for Cadherin-11 antagonist activity. For example, a composition comprising a Cadherin-11 protein can be used in a screen or binding assay to detect and/or identify agents that bind and antagonize the Cadherin-11 protein. Compositions suitable for use include, for example, cells that naturally express a Cadherin-11 protein (e.g., a synoviocyte), extracts of such cells, and recombinant Cadherin-11 protein.

An agent that binds a Cadherin-11 protein can be identified in a competitive binding assay, for example, in which the ability of a test agent to inhibit the binding of Cadherin-11 to a reference agent is assessed. The reference agent can be a full-length Cad-11 protein or a portion thereof that comprises the EC1 domain. The reference agent can be labeled with a suitable label (e.g., radioisotope, epitope label, affinity label (e.g., biotin and avidin or streptavadin), spin label, enzyme, fluorescent group, chemiluminescent group, dye, metal (e.g., gold, silver), magnetic bead) and the amount of labeled reference agent required to saturate the Cadherin-11 protein in the assay can be determined. The specificity of the formation of the complex between the Cadherin-11 protein and the test agent can be determined using a suitable control (e.g., unlabeled agent, label alone).

The capacity of a test agent to inhibit formation of a complex between the reference agent and a Cadherin-11 protein can be determined as the concentration of test agent required for 50% inhibition ($IC_{50}$ value) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents suitable for use in the method include molecules and compounds which specifically bind to Cadherin-11, e.g., an antibody that binds Cadherin-11.

An agent that antagonizes a Cadherin-11 protein can be identified by screening for agents that have an ability to antagonize (reduce, prevent, inhibit) one or more activities of Cadherin-11, such as, for example, a binding activity (e.g., homotypic Cad-11 binding). Such activities can be assessed using an appropriate in vitro or in vivo assay. Exemplary assays for Cadherin-11 activity have been described previously (Patel, S D, et al., *Cell* 124:_1255-1268 (2006); Lee et al., *Science* 315:1006-1010 (2007)).

Once a Cadherin-11 antagonist is identified, the ability of the Cadherin-11 antagonist to interfere with (e.g., reduce, inhibit, prevent) one or more biological functions or properties associated with Cadherin-11 activity in a cell can be assessed, for example, using a cell-based assay designed to measure a particular biological function or property associated with Cadherin-11. Biological functions and properties that are known to be associated with Cadherin-11 expression and/or activity include, but are not limited to, cell adhesion, cell migration, cell invasion, cell sorting, cell condensation, cell rearrangement, maintenance of tissue integrity and architecture, contact inhibition of cell proliferation and malignant transformation of cancer (e.g., tumor) cells (Kiener and Brenner, *Arthritis Res Ther.* 7(2):49-54 (2005)). In addition Cad-11 antagonists are shown herein to inhibit production of active MMPs by synoviocytes. Suitable assays for assessing one or more biological functions of cadherins are known to those of skill in the art (see, e.g., Patel, S D, et al., *Cell* 124: 1255-1268 (2006)) and include, for example, the cell aggregation assay described herein (see Exemplification, Materials and Methods section).

Methods of Therapy

Without wishing to be bound by any one theory, it is believed that the first about 35 amino acids (e.g., about 33 to about 37 amino acids) of the EC1 domain of Cad-11 are required for homotypic cadherin binding and that agents that specifically bind to this region of Cad-11 can effectively inhibit binding between Cad-11 molecules. Accordingly, such agents are useful in the treatment and prevention of inflammatory joint disorders (e.g., rheumatoid arthritis) associated with Cad-11 expression and activity in synoviocytes and other cell types in inflamed joints. Thus, one aspect of the present invention relates to a method for treating an inflammatory joint disorder in a mammalian subject comprising administering to the subject a therapeutically effective amount of a Cadherin-11 antagonist that binds a human Cadherin-11 EC1 domain peptide (SEQ ID NO:3).

Using the methods of the invention, an inflammatory joint disorder in a mammal (e.g., a human) can be treated by administering a Cadherin-11 antagonist of the invention (e.g., antibodies, fusion proteins, small molecules, nucleic acids, peptides, peptidomimetics) in an amount that is sufficient to provide a therapeutic benefit, for example, by inhibiting the aggregation of cells, or inhibiting the migration of cells, or inhibiting expression of active proteases or inflammatory molecules by cells, that express Cadherin-11 in an articulated joint (e.g., synoviocytes).

Accordingly, one aspect of the invention relates to a method for treating an inflammatory joint disorder in a mammalian subject comprising administering to the subject a therapeutically effective amount of a Cadherin-11 antagonist of the invention. The inflammatory joint disorder can be any disorder that is associated with or characterized by Cadherin-11 expression in cells (e.g., synoviocytes) of an articulated joint. Examples of inflammatory joint disorders that can be treated by the present invention include, but are not limited to, rheumatoid arthritis, psoriatic arthritis, Reiter's syndrome and ankylosing spondylitis. In a particular embodiment, the inflammatory joint disorder is rheumatoid arthritis.

In one aspect, a therapeutically effective amount of a Cadherin-11 antagonist is administered to a patient in need thereof. The amount of the Cadherin-11 antagonist to be administered (e.g., a therapeutically effective amount) can be determined by a clinician using the guidance provided herein and other methods known in the art and is dependent on several factors including, for example, the particular agent chosen, the subject's age, sensitivity, tolerance to drugs and overall well-being. For example, suitable dosages for Cad-11 antagonists that are antibodies can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment. Suitable dosages for a small molecule Cad-11 antagonist can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for Cadherin-11 antagonists that are proteins or peptides (linear, cyclic, mimetic), will result in a plasma concentration of the peptide from about 0.1 µg/mL to about 200 µg/mL. Determining the dosage for a particular agent, patient and cancer is well within the abilities of one skilled in the art. Preferably, the dosage does not cause, or produces minimal, adverse side effects (e.g., immunogenic response, nausea, dizziness, gastric upset, hyperviscosity syndromes, congestive heart failure, stroke, pulmonary edema).

A therapeutically effective amount of a Cadherin-11 antagonist can be administered alone, or in combination with one or more other therapeutic agents (e.g., anti-inflammatory agents). Suitable anti-inflammatory agents that are useful for treating inflammatory joint disorders, particularly RA, which can be administered in combination with Cad-11 antagonists of the invention, include, but are not limited to, (i) non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate); (ii) steroids (e.g., cortisone, dexamethasone, hydrocortisone, methylprednisolone, prednisolone, prednisone, triamcinolone); (iii) DMARDs, i.e., disease modifying antirheumatic drugs (e.g., cyclosporine, azathioprine, methotrexate, leflunomide, cyclophosphamide, hydroxychloroquine, sulfasalazine, D-penicillamine, minocycline, and gold); or (iv) recombinant proteins (e.g., ENBREL® (etanercept, a soluble TNF receptor), REMICADE® (infliximab, a chimeric monoclonal anti-TNF antibody), ORENCIA® (abatabacept, a soluble CTLA4 receptor), ACTEMRA® (Tocilizumab, a monoclonal antibody to the IL-6 receptor), and RITUXAN® (rituximab, a monoclonal antibody to CD20).

Thus, a Cadherin-11 antagonist can be administered as part of a combination therapy (e.g., with one or more other therapeutic agents). The Cad-11 antagonist can be administered before, after or concurrently with one or more other therapeutic agents. In some embodiments, the Cadherin-11 antagonist and other therapeutic agent can be co-administered simultaneously (e.g., concurrently) as either separate formulations or as a joint formulation. Alternatively, the agents can be administered sequentially, as separate compositions, within an appropriate time frame as determined by the skilled clinician (e.g., a time sufficient to allow an overlap of the pharmaceutical effects of the therapies). The Cadherin-11 antagonist and one or more other therapeutic agents can be administered in a single dose or in multiple doses, in an order and on a schedule suitable to achieve a desired therapeutic effect (e.g., a reduction in and/or inhibition of joint inflammation). Suitable dosages and regimens of administration can be determined by a clinician and are dependent on the agent(s) chosen, pharmaceutical formulation and route of administration, various patient factors and other considerations.

The effectiveness of a therapy (e.g., the reduction or elimination of joint inflammation and/or the prevention or inhibition of joint inflammation) can be determined by any suitable method (e.g., imaging (MRI, NMR)).

According to the methods of the invention, a therapeutically effective amount of a Cad-11 antagonist is administered to a mammalian subject to treat an inflammatory joint disorder. The term "mammalian subject" is defined herein to include mammals such as primates (e.g., humans) cows, sheep, goats, horses, dogs cats, rabbits, guinea pigs, rats, mice or other bovine, ovine, equine, canine feline, rodent and murine species.

Agents that are Cad-11 antagonists can be administered to a mammalian subject by a variety of routes. For example, the agent can be administered by any suitable parenteral or non-parenteral route, including, for example, topically (e.g., cream, ointment), or nasally (e.g., solution, suspension). Parenteral administration can include, for example, intraarticular, intramuscular, intravenous, intraventricular, intraarterial, intrathecal, subcutaneous, or intraperitoneal administration. The agent can also be administered orally (e.g., in capsules, suspensions, tablets or dietary), transdermally, intradermally, topically, by inhalation (e.g., intrabronchial, intranasal, oral inhalation or intranasal drops), transmucosally or rectally. Administration can be local or systemic as appropriate, and more than one route can be used concurrently, if desired. Localized administration of a Cad-11 antagonist can be achieved by intraarticular injection (e.g., direct injection of the agent into a joint). The preferred mode of administration can vary depending upon the particular agent chosen. However, systemic intravenous or subcutaneous administration is generally preferred for antibodies.

Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract. Delivery can be in vitro, in vivo, or ex vivo.

Agents that are proteins (e.g., fusion protein) can be administered via in vivo expression of recombinant protein. In vivo expression can be accomplished by somatic cell expression according to suitable methods (see, e.g., U.S. Pat. No. 5,399,346). Further, a nucleic acid encoding the protein can also be incorporated into retroviral, adenoviral or other suitable vectors (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

Nucleic acid-based Cadherin-11 antagonists (e.g., aptamers) can be introduced into a mammalian subject of interest in a number of ways. For instance, nucleic acids may be expressed endogenously from expression vectors or PCR products in host cells or packaged into synthetic or engineered compositions (e.g., liposomes, polymers, nanoparticles) that can then be introduced directly into the bloodstream of a mammalian subject (by, e.g., injection, infusion). Anti-Cadherin-11 nucleic acids or nucleic acid expression vectors (e.g., retroviral, adenoviral, adeno-associated and herpes simplex viral vectors, engineered vectors, non-viral-mediated vectors) can also be introduced into a mammalian subject directly using established gene therapy strategies and protocols (see e.g., Tochilin V. P. *Annu Rev Biomed Eng* 8:343-375, 2006; Recombinant DNA and Gene Transfer, Office of Biotechnology Activities, National Institutes of Health Guidelines).

Agents that are Cadherin-11 antagonists (e.g., small molecules) can be administered to a mammalian subject as part of a pharmaceutical or physiological composition, for example, as part of a pharmaceutical composition comprising a Cadherin-11 antagonist and a pharmaceutically acceptable carrier. Formulations or compositions comprising a Cadherin-11 antagonist or compositions comprising a Cadherin-11 antagonist and one or more other therapeutic agents (e.g., an anti-inflammatory agent) will vary according to the route of administration selected (e.g., solution, emulsion or capsule). Suitable pharmaceutical carriers can contain inert ingredients which do not interact with the Cadherin-11 antagonist. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying agents, solubilizing agents, pH buffering agents, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

The pharmaceutical agent can be administered as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2-ethylamino ethanol, histidine, procaine, etc. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counter-anion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium or potassium.

The present invention will now be illustrated by the following Examples, which are not intended to be limiting in any way.

EXEMPLIFICATION

Example 1

Identification of Fabs Having Binding Specificity for an Epitope within the N-Terminal 35 Amino Acids of the EC1 Domain of Human Cadherin-11

Materials and Methods

Western Blotting

Proteins were separated by SDS-PAGE and transferred to a nitrocellulose (NC) membrane using standard methods. Briefly NC membrane was rinsed with tris buffered-saline-tween (TBST) (8.8 g/L of NaCl, 0.2 g/L of KCl, 3 g/L of Tris base, 500 ul/L of Tween-20, pH to 7.4). The membrane was blocked with 4% BSA dissolved in TBST for hour at 22° C. The NC membrane was rinsed 3× for 5 min each with TBST. Mouse anti-human Cad-11 antibody was diluted to 0.5 µg/ml in TBST and the NC was incubated for 1 hour at 22° C. The NC membrane was rinsed 3× for 5 minutes each in TBST. Goat anti-mouse Ig antibody conjugated with horse radish peroxidase (HRP) was diluted to 1 µg/ml in TBST and the NC membrane was incubated in secondary solution for a minimum time of 1 hour @ room temperature (RT) at 22° C. The NC membrane was rinsed 3× for 5 min each in TBST. Signal was developed using standard HRP method.

ELISA

The antigen (either 5 µg/ml or 50 µg of Cad-11-EC-1-Fc or 5 µg/ml of Cadherin peptide) was diluted in a buffer and used to coat the plates overnight at 4° C. The plates were washed and then blocked with 1.5% BSA, 5% low fat milk powder in PBS Dilution buffer: 1.5% BSA, 2.5% low fat milk powder, 0.1% Tween-20 in PBS. The plates were then incubated with bacterial lysate containing the anti-Cad-11 human fAbs or purified anti-Cad-11 human fAbs for 1 hr. After washing, the secondary antibody (Cy5-conjugated a-hu-Fab diluted 1/100) was applied for 25 min. The plates were then washed and the resulting fluorescence read.

Results

Figure 1A:
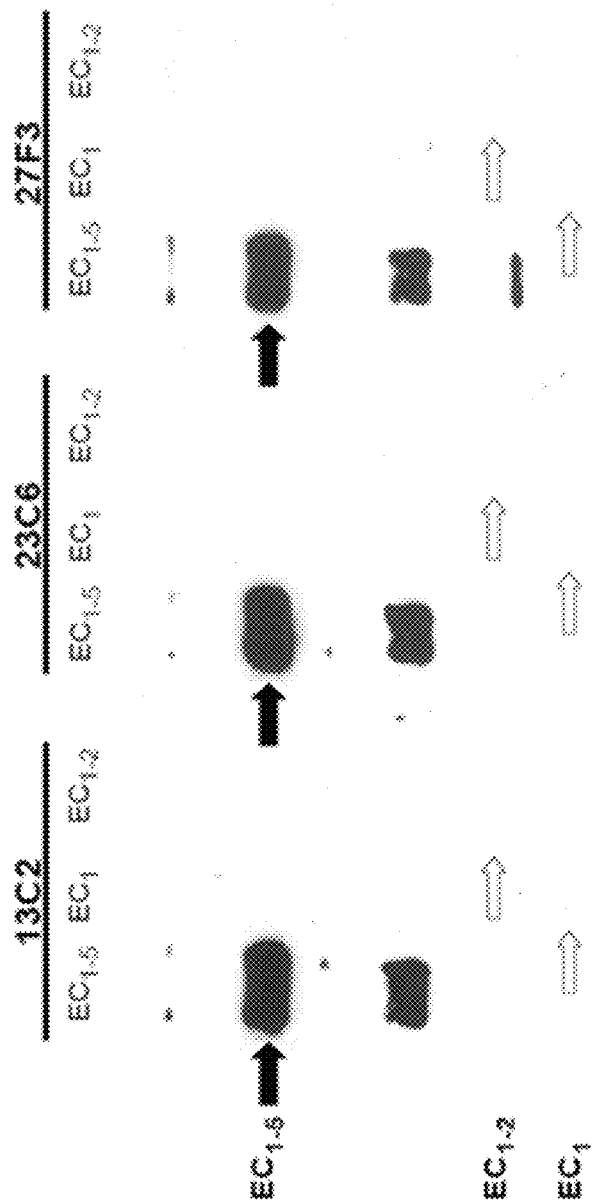
FIG. 1A is a Western blot showing detection of a Cadherin-11-EC1-5-Fc fusion protein using anti-Cad-11 antibodies 23C6, 13C2 and 27F3 (see solid arrows). These antibodies did not recognize the Cadherin-11-EC1-Fc and Cadherin-11-EC1/2-Fc fusion proteins that were also present on the membrane (see open arrows for positions of the Cadherin-11-EC1-Fc and Cadherin-11-EC1/2-Fc proteins on the blot).
Figure 1B:
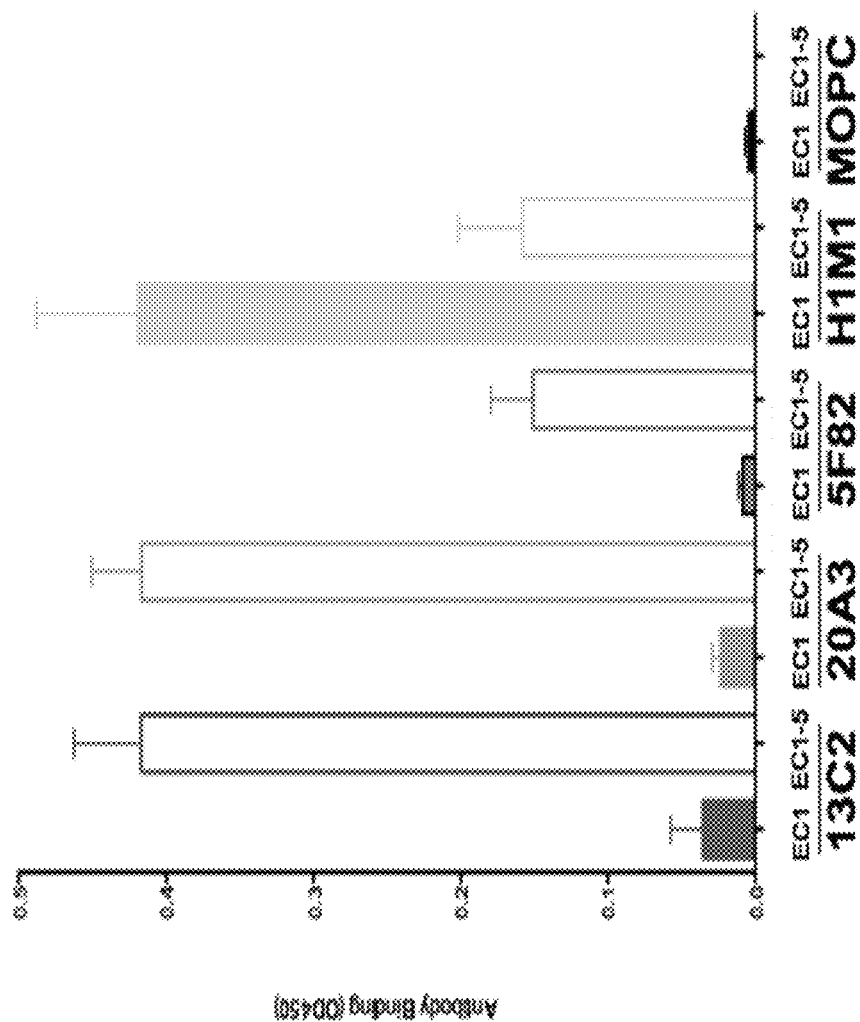
FIG. 1B is a graph depicting the binding of public Cadherin-11 antibodies 13C2, 23C6 and 5F82 to human Cad-11-EC1-5-Fc fusion protein, but not the Cad-11-EC1-Fc fusion protein, as determined by ELISA. In contrast, the EC1 antibody H1M1 binds both Cad-11-EC1-Fc fusion protein and the Cad-11-EC1-5-Fc fusion protein.

Three sets of previously reported Cadherin-11-specific antibodies were tested for an ability to bind to the EC1 domain of human Cadherin-11. These antibodies included antibodies that were raised against a mouse Cadherin-11-Fc fusion protein immunogen in Cadherin-11 knock-out or deficient mice (Lee et al., *Science* 315:1006-1010 (2007)), antibodies that were raised in Cadherin-11 wild type mice against a human Cadherin-11-Fc fusion protein immunogen that had been produced in CHO cells (Valencia et al., *J. Exp. Med.* 200(12):1673-1679 (2004)), and antibodies that were raised in Cadherin-11 wild type mice against a bacterially-produced protein containing the EC1-3 domains of human Cadherin-11. These antibodies were tested by western analysis for an ability to bind fusion proteins that contained only the EC1 domain of human Cad-11(Cadherin-11-EC1-Fc), the EC1 and EC2 domains of Cad-11 (Cad11-EC1/2-Fc) or all 5 EC domains of Cad-11 (Cadherin-11-EC1-5-Fc). None of the antibodies tested recognized the EC1-Fc or the EC1-2-Fc fusion proteins on a Western blot (FIG. 1A). However, antibodies from each of the three sets tested recognized the human Cad-11-Fc fusion protein that included extracellular domains 1 through 5 (FIG. 1B). These results indicate that the tested antibodies did not bind to the EC1 or EC2 domains of human Cad-11, but recognized epitopes elsewhere in the extracellular region of this protein.

The available published anti-Cad11 antibodies that bind Cad11 expressing cells, 13C2, 23C6, 5F82 (Lifespan Science) and 283416 (R&D Systems), as well as the Cad11 EC1-binding antibody H1M1, and the control antibody, MOPC, were tested by ELISA for the ability to bind fusion proteins that contained only the EC1 domain of human Cad-11 (Cadherin-11-EC1-Fc) or all 5 EC domains of Cad-11 (Cadherin-11-EC1-5-Fc). None of the available published anti-Cad11 antibodies tested recognized the EC1-Fc (FIG. 1B, open bars) (data for 283416 is not shown here). However, the Cad11 EC1 binding H1M1 antibody bound both the Cadherin-11-EC1-Fc and Cadherin-11-EC1-5-Fc (FIG. 1B closed bar). The control MOPC antibody bound neither fusion protein. These results indicate that the available published anti-Cad11 antibodies do not bind to the EC1 domain of human Cad-11, but recognized epitopes elsewhere in the extracellular region of this protein.

To create an antibody specific for an epitope within the N-terminal 35 amino acids of the EC1 domain of human Cadherin-11, a phage display library (MorphoSys AG) encoding human Fabs was screened. Candidate Fabs were identified using two selection criteria—a positive selection for binding to a peptide that included the first 35 amino acids of the human Cadherin-11 EC1 domain, and a negative selection for binding to corresponding peptides from the EC1 domains of two closely related and highly homologous cadherins, Cadherin-8 and MN-Cadherin (FIG. 2). ELISA was used to assess binding.

Figure 3:
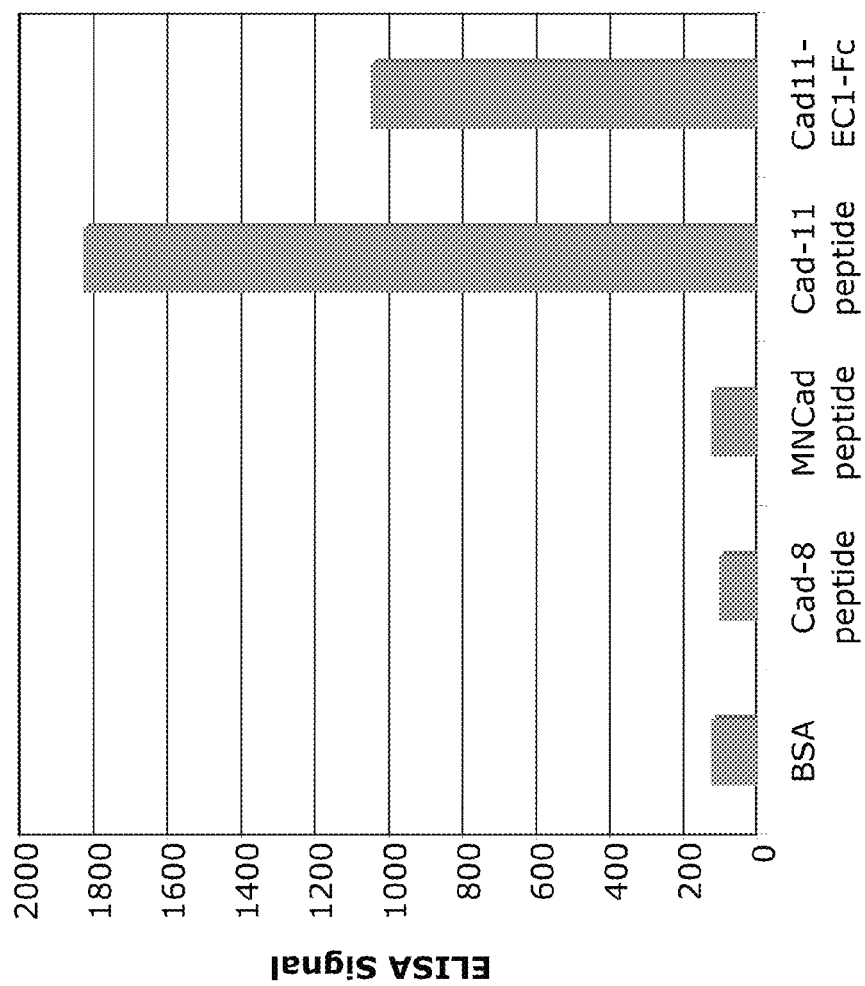
FIG. 3 is a graph depicting the binding of a Cadherin-11-binding Fab to a human Cad-11 EC1 domain peptide as well as the Cad-11-EC1-Fc fusion protein, but not the Cad-8 or MN-Cad EC1 domain peptides, as determined by ELISA. Clone 7 demonstrated significant binding to the Cad-11 EC1 domain peptide and fusion protein, but not the MN-Cad or Cad-8 EC1 domain peptides.

Two screens were conducted. In the first screen, 96 Fab clones that bound the Cadherin-11 EC1 peptide were identified by ELISA. Seven (7) candidate Fabs bound the Cad-11 EC-1 peptide; however, only two of these bound to both EC-1 peptide and the EC1-2-Fc fusion protein. One of these two Fabs also bound to MN-Cad peptide. Accordingly, only one of the seven Fab clones specifically bound the EC1-Fc fusion protein, but did not bind to both MN-Cad and Cadherin-8 EC1 domain peptides. In a second screen, similar results were observed, as only 1 of 96 Fabs (clone F9) showing specificity for the Cadherin-11 EC1 peptide and EC1-2-Fc fusion protein, failed to bind MN-Cad and Cadherin-8 EC1 domain peptides (FIG. 3). The majority of the Cad-11 EC1 domain-binding Fabs tested showed cross reactivity with the MN-Cad peptide, which contains an EEY CAR sequence that overlaps with the EEY CAR sequence of Cad-11.

Example 2

A Fab that Binds the EC1 Domain of Cadherin-11 Inhibits Cad-11 Mediated Cell Aggregation in an In Vitro Assay Materials and Methods
In Vitro Cadherin-11 Aggregation Assay 431-D cells grow in suspension and do not normally express any cadherins and do not aggregate. 431-D-11 cells have been genetically modified to express Cad-11. When 431-D-11 cells are incubated in media alone and they begin to aggregate over 40 min and the clumps of cells settle to the bottom of well and the remaining non-aggregated cells in suspension can be measured and the percentage of aggregated 431-D-11 calculated. For the aggregation assay, 431-D-11 cells (D-11 cells) were grown to sub-confluence in a flask and then were removed from the flask using 0.05% Trypsin plus 0.53 mM EDTA. Approximately $2 \times 10^6$ 431-D-11 cells were added to 2 ml of SME media (Dulbecco's Modified Eagle's Medium-high glucose, 0.1M Hepes pH 7.4 and 5 U/ml DNAse) and were preincubated for 15 min on ice, either in the absence or presence of a test agent (e.g., antibody, Fab, fusion protein). After pre-incubation with the test agent, the cells were transferred to a round bottom well on a 24-well plate and incubated at 37° C. while rotating at 130 rpm on a rotary shaker. As cells aggregate they sink to the bottom of the well. At 0 min and 40 min, 200 µl from the middle of the sample were removed from the well and mixed with 25 µl of 8% glutaraldehyde to fix the cells. 200 µl of the fixed sample of cells were added to 9.8 ml of Coulter Counter isotonic saline solution and counted using a Coulter Counter set at the 8 µm to 24 µm threshold. 3 cell counts per sample were recorded. The percentage of cell decrease or aggregated cells at 40 min. compared to the percentage at the 0 min. time point was calculated.

Results

Figure 4:
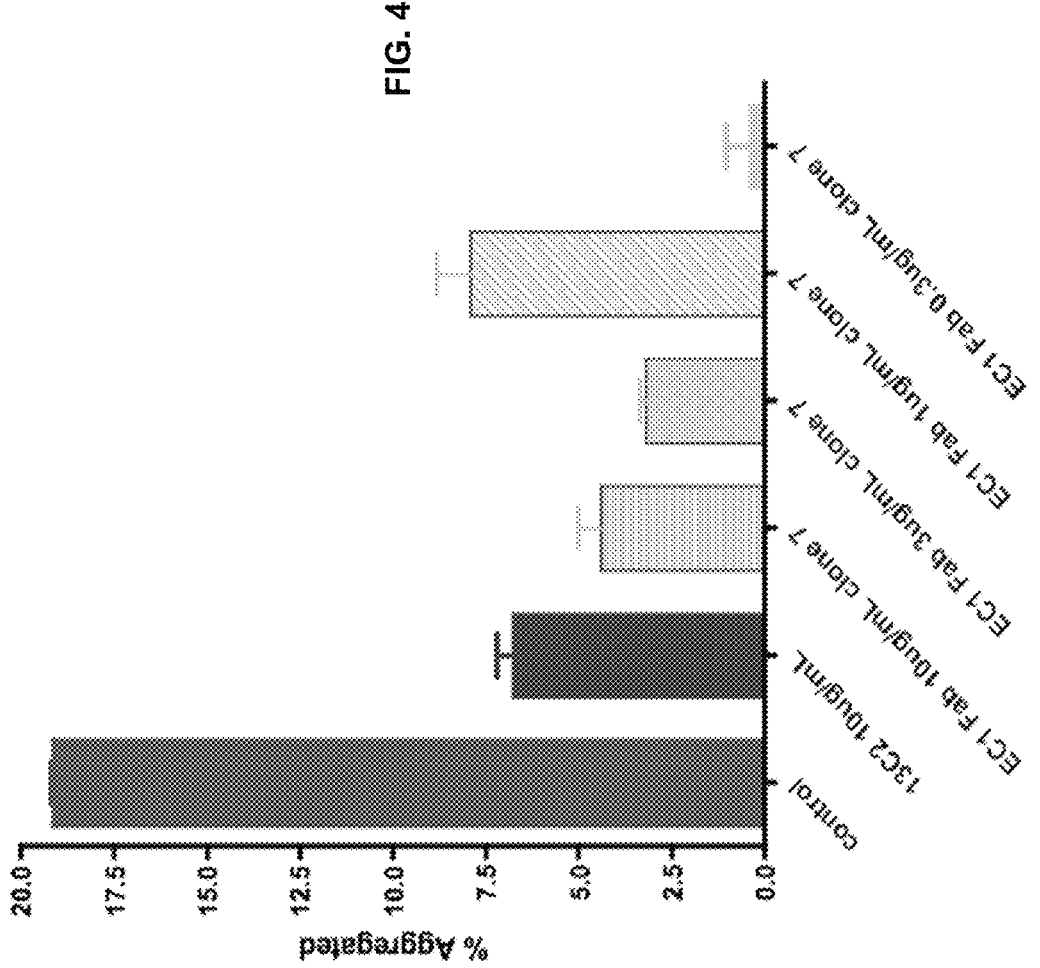
FIG. 4 is a graph depicting data from an in vitro Cad-11 cell aggregation assay. Cad-11 antagonists added to the media, such as a Fab made from the anti-Cad-11 antibody 13C2, or varying concentrations of an anti-Cadherin-11 EC1 Fab directed to the first 35 amino acids of the EC1 domain of Cadherin-11 (designated EC1 Fab clone 7), block Cad-11 mediated 431-D-11 cell aggregation. The anti-Cadherin-11 EC1 Fab (clone 7) inhibited aggregation of A-431-D-11 epidermoid carcinoma cells at all concentrations tested in a range of 0.3 µg/ml to 10 µg/ml. In contrast, the Fab made from the 13C2 anti-Cadherin-11 antibody only inhibited cell aggregation at a concentration of 10 µg/ml.
Figure 5:
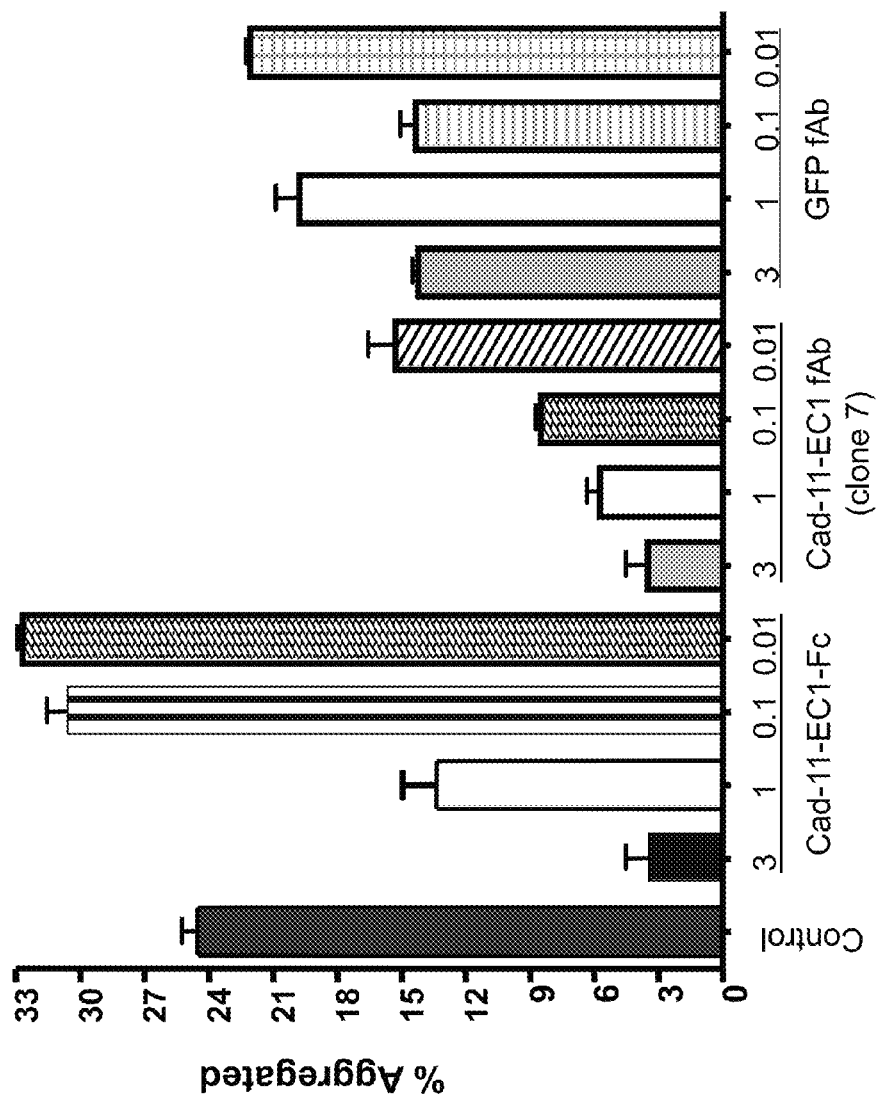
FIG. 5 is a graph depicting data from a second in vitro Cad-11 cell aggregation assay. Percent aggregation of 431-D-11 cells is shown at 40 min. after addition of either SME media (designated control), varying concentrations of a fusion protein comprising the EC1 domain of Cad-11 fused to the human IgG2 hinge, CH2 and CH3 domains (designated Cad-11-EC1-Fc), varying concentrations of an anti-Cadherin-11 EC1 Fab directed to the first 35 amino acids of the EC1 domain of Cadherin-11 (designated Cad-11 EC1 Fab) or varying concentrations of a control anti-green fluorescent protein (anti-GFP) Fab (designated GFP fAb). The anti-Cadherin-11 EC1 Fab (clone 7) inhibited aggregation of Cad-11 expressing 431-D-11 cells at concentrations of 3 µg/ml, 1

A candidate Fab (clone F9) having binding specificity for an epitope within the N-terminal 35 amino acids of the Cadherin-11 EC1 domain, which does not bind the EC1 domains of MN-Cad or Cad-8, was tested for an ability to inhibit Cad-11 mediated cell aggregation using an in vitro Cadherin-11 cell aggregation assay. The candidate Fab significantly inhibited Cadherin-11 mediated aggregation of cells at concentrations of 1 µg/ml or lower (FIGS. 4 and 5). In contrast, a Fab made from the 13C2 antibody that binds to an epitope in the extracellular region of Cad-11 outside the EC1/2 domains inhibited Cadherin-11 aggregation only at a concentration of 10 µg/ml, suggesting that the F9 Fab inhibits Cad-11 activity more effectively at lower concentrations than antibodies which bind to other portions of the extracellular domain of Cad-11.

Cad-11 mediated cell aggregation was also inhibited by various anti-Cadherin-11-EC1 domain Fabs that were specific for either Cad-11 alone, Cad-11 and Cad-8, Cad-11 and MN-Cad, or Cad-11, Cad-8 and MN-Cad (FIGS. 6 and 7). All cadherin-EC1-domain specific Fabs that were tested inhibited cell aggregation in vitro relative to the control samples (e.g., SME medium (FIG. 6), a Fab specific for GFP (FIG. 7).

Example 3

Generation of Cadherin-11/Immunoglobulin Fusion Proteins Containing the EC1 Domain of Human Cadherin-11

The Cadherin-11 EC1 region was prepared from a vector encoding the full length human Cadherin-11 cDNA (human Cad-11 cloned into the Not1 and Kpn-1 sites of the Invitrogen pCEP4® vector) using polymerase chain reaction (PCR) performed under standard conditions using the following oligonucleotide primers to introduce EcoR1 and BglII sites (see underlined sequences in forward and reverse primers, respectively) into the amplified product:

```
Forward Primer:
                                            (SEQ ID NO: 8)
    ttttttttttgaattcatgaaggagaactactgtttacaagc
              EcoR1

Reverse Primer:
                                            (SEQ ID NO: 9)
    ttttttttagatctctggaccttgacaatgaattccgacgg
              BglII
```

The amplified product was digested with restriction enzymes EcoR1 and BglII, and the digestion product was isolated and ligated into the pFUSE-hIgG2e1-Fc1 vector (InvivoGen) using the corresponding EcoR1 and BglII sites. TOP10 competent bacteria (Invitrogen) were transformed as described by the manufacturer with the ligation product and bacteria with the Cadherin-11-EC1-Fc plasmid were selected with zeomycin. Cadherin-11-EC1-Fc plasmid was isolated, sequenced and then used to transiently transfect 293F cells. Conditioned media was collected and the Cadherin-11-EC1-Fc fusion protein (SEQ ID NO:9) was purified using tangential flow filtration followed by isolation on a 50/50 mix protein A/protein G column equilibrated in 20 mM HEPES pH 7.4, 137 mM NaCl, 3 mM KCl and 1 mMCaCl2. The purified Cadherin-11-EC1-Fc fusion protein was eluted from the column using 0.1 M Glycine (pH 3) and 1 mM CaCl2 and into tubes containing 200 μl of 1M Tris pH 7.4, and 1 mM CaCl$_2$. The eluates with the Cad-11 fusion protein were then dialyzed against 20 mM Hepes (pH 7.4), 137 mM NaCl, 3 mM KCl and 1 mM CaCl$_2$. The size of the protein was confirmed by SDS PAGE (FIG. 10) and identity was confirmed by Western analysis using an antibody that recognizes the human Fc region (FIG. 11) and N-terminal sequencing (not shown). Cad-11-EC1-2-Fc was produced using techniques and conditions similar those described above.

Example 4

A Cad-11-EC1-Fc Immunoglobulin Fusion Protein Inhibits Cad-11 Mediated Cell Aggregation in an In Vitro Assay Materials and Methods
Cell Invasion/Migration into a Matrigel Plug FLS migratory activity was assessed in Matrigel ECM-coated transwells in FLS media (Dulbecco's Modified Eagle's Medium-high glucose [Sigma #D7777], 10% Fetal Bovine Serum [Benchmark #100-106], 1% Pencillin-Streptomycin [Gibco 315140-122], 1% L-Glutamine [Gibco #25030], 0.5% Gentamicin [Gibco #15710-064]. Human FLS cell suspensions in FLS medium containing 1×10$^4$ cells were added to the control insert or matrigel coated insert set in the well of a 24-well plate containing 0.750 mL of FLS medium. The plates were then incubated in a humidified tissue culture incubator at 37° C., 5% CO$_2$ atmosphere for 22 hours.

To calculate the number of cells that migrated, non-invading cells were removed from the upper surface of the membrane of control inserts by wiping with a cotton swab. A second wipe using a cotton swap wetted with FLS medium is repeated. Control inserts were then fixed and stained using a differential staining kit [Fisher #122-911]. Inserts are allowed to dry and cells are counted in 4 quadrants of the control insert using a microscope with a 10× objective. Triplicate inserts are counted and the totals averaged.

To calculate the number of cells that invaded the matrigel inserts, non-invading cells were gently removed from the surface of the matrigel insert by wiping with a cotton swab. A second wipe using a cotton swap wetted with FLS medium is repeated. Inserts were then fixed and stained using a differential staining kit [Fisher #122-911]. Inserts are allowed to dry and cells are counted in 4 quadrants of the control insert using a microscope with a 10× objective. Triplicate inserts are counted and the totals averaged.

Results

Cad-11-EC1-Fc significantly inhibited cell aggregation at a concentration of 3 μg/ml, while the full length Cad-11-EC1-5-Fc protein containing all 5 EC domains of human Cad-11 inhibited Cad-11 mediated aggregation at a concentration of 100 μg/ml (FIG. 13). These data show that the Cad-11-EC1-Fc immunoglobulin fusion protein effectively inhibits Cad-11 mediated cell aggregation in an in vitro assay.

In addition, the ability of the Cad-11-EC1-Fc immunoglobulin fusion protein to inhibit the invasion of human fibroblast like synoviocytes (FLS) into a matrigel plug was tested in vitro. Invasion of the FLS into matrigel is a complex process that involves the expression of MMP1, MMP-3, MMP-13, serine proteases, and other proteins by the FLS to degrade the matrigel as well as the migration of the FLS into matrigel. In a separate assay we saw no inhibition of migration of FLS through a normal fiber insert. This suggests the impact of the EC-Fc or 13C2 mAb is to inhibit the degradation of the matrigel (a surrogate for joint cartilage). Both the Cad-11-EC1-Fc and murine anti-Cad-11 mAb 13C2 inhibited FLS invasion into a matrigel plug in two independent experiments.

Example 5

Generation of Antibodies Against an EC1 Domain Peptide of Human Cadherin-11

Materials and Methods

Balb/c mice were immunized bi-weekly in the foot pad nine times over a one month period with 0.01 mg of a peptide corresponding to the first 33 amino acids of the human Cad-11 EC1 domain (GWVWN QFFVI EEYTG PDPVL VGRLH SDIDS GDG (SEQ ID NO:10)), covalently linked to BSA. This peptide is referred to herein as Peptide 4. Spleens from the immunized mice were harvested and fused with a murine fusion partner, P3X63-Ag8.653, to create antibody-producing hybridomas. The hybridomas were expanded and subcloned at either 10, 3 or 0.5 cells/well, and the anti-Cad-11 antibody-containing media from the hybridomas were screened in an ELISA for the ability to specifically bind Cad-11 EC1-2 domain-containing protein produced in bacteria. Anti-Cad-11 antibody-containing media from these Peptide 4 hybridomas were screened concurrently for the absence of binding to proteins encompassing the EC1-2 domains of human Cad-8 and MN-Cadherin. 96-well EIA plates were coated overnight at 4° C. with 0.05 ml of 0.0 to 0.3 mg/ml of each of the EC1-2 Cad proteins and then washed several times with saline buffer. Plates were then blocked with 0.25 ml of casein-PBS buffer and washed several times with saline buffer. Hybridoma media containing the anti-Cad-11 antibody were incubated neat in each well for 1 hr at 22° C. and then washed twice with PBS-Tween (0.05%). 100 μl of a 1/1000 dilution of a goat anti-mouse IgG secondary antibody were added to each well, incubated for 30 min at 22° C., and then washed twice with PBS-Tween (0.05%). 100 µl/well of room temperature TMB (3,3',5,5'-tetramethylbenzidine) reagent was added to each well and color was allowed to develop for 5 min at 22° C. The reaction was stopped with 100 µl of room temperature 2N sulfuric acid and the plate was read at 450 nm on a Wallac 1420 microplate reader.

The specificity of H1M1 and H14 anti-Cad-11 antibodies was tested further using an ELISA against the first 33 amino acids of the EC1 domains of Cad-11, Cad-7, Cad-8, Cad-20, Cad-24, Cad-9, Cad-18, and MN-Cad. Peptides corresponding to the region of Cad-7, Cad-8, Cad-20, Cad-24, Cad-9, Cad-18, MN-Cad that overlapped with the G1-G33 region of the Cad-11 EC1 domain were synthesized and conjugated to biotin. 100 µl of a 30 ng/ml solution of each of these peptides in PBS-Tween (0.05%) were incubated in each well of a 96-well Netravidin plate for 2-3 hrs at 4° C. and then washed twice with PBS-Tween (0.05%). Various concentrations of the anti-Cad-11 antibody were incubated in each well for 1 hr at 22° C. and then washed twice with PBS-Tween (0.05%). 100 µl of a 1/1000 dilution of a goat anti-mouse IgG secondary antibody were added to each well, incubated for 30 min at 22° C., and then washed twice with PBS-Tween (0.05%). 100 µl/well of room temperature TMB (3,3',5,5'-tetramethylbenzidine) reagent was added to each well and color was allowed to develop for 5 min at 22° C. The reaction was stopped with 100 µl of room temperature 2N sulfuric acid and the plate was read at 450 nm on a Wallac 1420 microplate reader.

Media from wells containing positive anti-Cad-11 antibody hybridomas were tested for the ability to bind to Cad-11 expressing cells. Frozen Cad-11-expressing 431D cells were thawed and washed twice in Hanks Balanced Saline Solution (HBSS) containing $Ca^{2+}$ (0.137 M NaCl, 5.4 mM, KCl 0.25, mM $Na_2HPO_4$, 0.44 mM $KH_2PO_4$, 1.3 mM $CaCl_2$, 1.0 mM $MgSO_4$ and 4.2 mM $NaHCO$) and then resuspended at $10^6$ cells/ml in HBSS containing $Ca^{2+}$. $10^5$ cells/well were stained with either a 50% or 16% anti-Cad-11 antibody media for 45 min on ice, washed twice in HBSS containing $Ca^{2+}$, stained with a secondary goat anti-mouse IgG antibody conjugated with phytoerytherin (Jackson ImmunoResearch, West Grove, Pa.) a concentration of 1% for 45 min on ice and then washed again twice in HBSS containing $Ca^{2+}$. Cells were then resuspended in 400 µl of HBSS containing $Ca^{2+}$ and 1% formaldehyde and subsequently analyzed on a FACScalibur (Becton Dickenson, Franklin Lakes, N.J.) for PE positive cells.

Results

Anti-Cad-11 antibody-containing media from the Peptide 4 hybridomas bound to the Cad-11 EC1-2 protein (FIG. 16, HL vs CAD11), but not proteins containing the EC1-2 domains of Cad-8 and MN-Cad (FIG. 16, HL vs CAD8 and HL vs MNCAD, respectively). Control hybridoma media did not bind any of the cadherin proteins tested (FIG. 16, Media vs CAD11, Media vs CAD8, and Media vs MNCAD). These data demonstrate the presence of Cad-11 specific antibodies to Peptide 4 in the hybridomas.

Two Peptide 4 hybridomas, referred to herein as H1M1 and H14, bound to cells expressing human Cad-11 protein (FIGS. 17A-C and 17G-I), but not to non-Cad-11 control 431-D cells (FIGS. 17D-17F). The hybridoma cell line referred to as H1M1 has the A.T.C.C. designation number PTA-9699, having been deposited on Jan. 8, 2009. The hybridoma cell line referred to as H14 has the A.T.C.C. designation number PTA-9701, having been deposited on Jan. 9, 2009. These hybridomas contain anti-Cad-11 antibodies that recognize both Peptide 4 and Cad-11-expressing cells in vitro. The binding of these antibodies to Cad-11-expressing cells was shown to titrate with the amount of Peptide 4 antibody that was used, as shown in the plots of the titration of H1M1 (FIG. 18A) and H14 (FIG. 18B) versus the intensity of cell staining from the mean fluorescence intensity (MFI).

The H1M1 and H14 Peptide 4 anti-Cad-11 antibodies demonstrated >100-fold higher binding to Cad-11 than to any of the other cadherins tested, which included Cad-7, Cad-8, Cad-20, Cad-24, Cad-9, Cad-18, and MN-Cad. In most cases, no binding of H1M1 and H14 anti-Cad-11 antibodies to the other cadherins was observed. The anti-Cad-11 antibody H14 showed strong binding to Cad-11 (FIG. 19A), with 468-fold lower binding to Cad-8 (FIG. 19A), and virtually no binding to Cad-7, MN-Cad, Cad-9, Cad-18, Cad-20 or Cad-24 (FIG. 19B). Similarly, the anti-Cad-11 antibody H1M1 showed strong binding to Cad-11 (FIG. 20), with 365-fold lower binding to Cad-8 (FIG. 20), and no binding to Cad-7, MN-Cad, Cad-9, Cad-18, Cad-20 or Cad-24 (data not shown).

Example 6

The Anti-Cad-11 EC1 Domain Antibodies H1M1 and H14 Bind Epitopes in the Cad-11 EC1 Domain that Include the Amino Acid Sequence GPDP Materials and Methods To determine the epitope within the Cad-11 EC1 domain that the Peptide 4 Cad-11 EC1 antibodies H1M1 and H14 bind, four different peptides spanning the first 37 amino acids of the EC1 region (see FIG. 22) were immobilized in an ELISA format and the ability of the H1M1 and H14 antibodies to bind each of the four peptides was determined. 96-well Reactibind plates were coated overnight at 4° C. with 0.3 ng/well of Peptide 1 (amino acids G1-P18 of the Cad-11 EC1 domain), 0.3 ng/well of Peptide 2 (amino acids G15-N34 of the Cad-11 EC1 domain), 0.3 ng/well of Peptide 3 (amino acids V19-Y37 of the Cad-11 EC1 domain), 0.3 ng/well of the immunogen Peptide 4 (amino acids G1-G33 of the Cad-11 EC1 domain), 20 ng of a fusion protein including the entire EC1 domain (EFL), or 20 ng of control human Ig (Fc-block). The wells were washed twice with PBS-Tween (0.05%), blocked with casein in $dH_2O$ for 3 hrs at 22° C. and then washed again twice with PBS-Tween (0.05%). Various dilutions of the different Peptide 4 CAD-11 EC1 domain antibodies were transferred to the peptide- or protein-coated wells, incubated for 45 min at 22° C. and then washed twice with PBS-Tween (0.05%). 100 µl of a 1/1000 dilution of goat anti-mouse IgG secondary antibody (Jackson ImmunoResearch, West Grove, Pa.) were added to each well, incubated for 30 min at 22° C. and then washed twice with PBS-Tween (0.05%). 100 µl/well of room temperature TMB reagent was added to each well and color was allowed to develop for 5 min at 22° C. The reaction was stopped with 100 µl of room temperature 2 N sulfuric acid and the plate was read at a wavelength of 450 nm on a Wallac 1420 microplate reader.

Results

The Peptide 4 anti-Cad-11 antibodies H1M1 at 1:11 (FIG. 21A) and H14 at 1:23 (FIG. 21B) both bound the Peptide 4 (PEP4) immunogen, as well as the EC1 domain fusion protein (EFL), in the ELISA as indicated by elevated OD450 plate readings relative to the control. Neither of these antibodies bound to the human IgG control (Fc block). In addition, both antibodies bound Peptide 2 (PEP2), but not Peptide 1 (PEP1) or Peptide 3 (PEP3), in the ELISA (FIGS. 21A and 21B).

These results suggest that the anti-Cad-11 EC1 domain antibodies H1M1 and H14 bind a common epitope in Peptides 2 and 4 that is not present in the overlapping Peptide 3. Amino acids shared by Peptides 2 and 4 that are upstream of Peptide 3 are highlighted in the boxed region shown in FIG.

22. These four amino acids, GPDP (SEQ ID NO:11), beginning at G15 of the Cad-11 EC1 domain, are likely part of the epitope recognized by the H1M1 and H14 antibodies.

Example 7

The Anti-Cad-11 EC1 Domain Antibodies H1M1 and H14 Inhibit Aggregation of Cad-11-Expressing Cells In Vitro Materials and Methods To assess the ability of the Cad-11 antibodies to inhibit Cad-11 mediated cell aggregation, 30 µg/ml of the H1M1 Peptide 4 antibody was cultured with 75,000 Cad-11 expressing A-431-D epidermoid carcinoma cells in 0.5 ml of DMEM-high glucose, 20 mM Hepes pH 7.4, 10% FCS and 10 U/ml DNAse in a 24-well round bottom polypropylene plate. The 24-well plates were placed on a rotating platform at approximately 60 rpm and incubated with 5% $CO_2$ overnight at 37° C. The next day, cell aggregation was assessed after photographing the plates at 100× (for H1M1 experiment) or 40× (for H14 experiment) magnification.

Results

In the presence of a control isotype antibody (30 µg/ml), the Cad-11-expressing cells formed large masses (FIG. 23A), while the parental Cad-11 negative cells remain as single or double cell groups (FIG. 23C). The H1M1-treated Cad-11 cells remained as small clumps of cells (FIG. 23B) that did not progress to form the large masses obtained using the control antibody.

Using the same assay, the anti-Cad-11 antibody H14 was also shown to inhibit Cad-11-mediated aggregation. While the parental Cad-11-expressing cells formed large clusters of aggregated cells (FIG. 24A), the H14 antibody (FIG. 24B) inhibited aggregation at a concentration of 30 µg/ml, as cell clusters were small and infrequent. These results indicate that the anti-Cad-11 antibodies H1M1 and H14 inhibit Cad-11-mediated cell aggregation in vitro.

Example 8

The Anti-Cad-11 EC1 Domain Antibodies, H1M1 and H14, Inhibit Arthritis-Associated Joint Swelling In Vivo in a Murine Model of Rheumatoid Arthritis Materials and Methods Study 1—Six-week-old male C57/B16 mice were injected with 150 µl of KBN sera on day 0 and day 2. KBN sera-treated mice received either saline injections (FIG. 25, unfilled triangles) or were treated with different doses of the H1M1 anti-Cad-11 EC1 antibody. Treatment regimens included dosing on day 0 with 0.5 mg of antibody/mouse and every second day (q2d) thereafter with 0.1 mg of antibody/mouse (0.5 mg+0.1 mg) (FIG. 25, filled triangles); dosing on day 0 with 0.5 mg of antibody/mouse (0.5 mg) (FIG. 25, diamonds); dosing every second day (q2d) with 0.1 mg of antibody/mouse (0.1 mg+0.1 mg) (FIG. 25, squares); or dosing every second day (q2d) with 0.3 mg of antibody/mouse (0.3 mg+0.3 mg) (FIG. 25, circles). The control group consisted of 5 mice and the treatment group consisted of 7 mice. Arthritis-associated joint swelling was determined by caliper measurements taken every second day.

Study 2—Six-week-old male C57/B16 mice were injected with 150 µl of KBN sera on day 0 and day 2, and then were treated with either saline every second day (q2d) (FIG. 26, triangles), or one of the anti-Cad-11 antibodies, H1M1 (FIG. 26, squares) or H14 (FIG. 26, circles), at 0.3 mg/dose q2d. The control group consisted of 5 mice and the treatment group consisted of 7 mice. Arthritis-associated joint swelling was determined by caliper measurements taken every second day.

Results

Study 1—The H1M1 anti-Cad-11 antibody inhibited joint swelling relative to the control mice. The greatest inhibition of arthritis-associated joint swelling was observed by dosing KBN-treated mice with 0.3 mg of H1M1 antibody every second day (FIG. 25, circles).

Study 2—Both of the anti-Cad-11 antibodies inhibited joint swelling relative to the control. In this study, the H14 antibody significantly delayed the onset of arthritis compared to the control animals (FIG. 27). All mice in the control group developed arthritis by day 3, while the H14-treated mice required 6 days before all of the animals developed arthritis.

These studies indicate that antibodies against the EC1 domain of human Cad-11 can inhibit the development and severity of arthritis in vivo.

Example 9

Generation of Antibodies Against Another EC1 Domain Peptide of Human Cadherin-11

Materials and Methods

Balb/c mice were immunized bi-weekly in the foot pad nine times over a 1 month period with 0.01 mg of peptide V19-Y37 (VL VGRLH SDIDS GDGNI KY (SEQ ID NO:12)), corresponding to 19 amino acids of the human Cad-11 EC1 domain, covalently linked to BSA. This peptide is referred to herein as Peptide 3. Spleens from the immunized mice were harvested and fused with a murine fusion partner P3X63-Ag8.653, to create antibody-producing hybridomas. These hybridomas were expanded and the anti-Cad-11 antibody-containing media from the hybridomas were screened for the ability to bind to a protein corresponding to the EC1-2 domain of Cad-11, which was produced in bacteria. The anti-Cad-11 antibody-containing media from these Peptide 3 hybridomas were screened concurrently for the absence of binding to proteins encompassing the EC1-2 domains of Cad-8 and MN-Cadherin. 96-well EIA plates were coated overnight at 4° C. with 0.05 ml of 0 to 300 mg/ml of one of each of the EC1-2 Cad proteins, or CHO cell produced EC1-Fc fusion protein, and then washed several times with saline buffer. Plates were then blocked using 0.25 ml of casein-PBS buffer and subsequently washed several times with saline buffer. Hybridoma media containing the Peptide 3 anti-Cad-11 antibodies were incubated neat in each well for 1 hr at 22° C. and then washed twice with PBS-Tween (0.05%). 100 µl of a 1/1000 dilution of a goat anti-mouse IgG secondary antibody were added to each well, incubated for 30 min at 22° C., and then washed twice with PBS-Tween (0.05%). 100 µl/well of room temperature TMB (3,3',5,5'-tetramethylbenzidine) reagent was added to each well and color was allowed to develop for 5 min at 22° C. The reaction was stopped with 100 µl of room temperature 2N sulfuric acid and the plate was read at 450 nm on a Wallac 1420 microplate reader.

Media from the Peptide 3 hybridomas were also tested for the ability to bind to human Cad-11 protein expressed on cells. Frozen Cad-11-expressing 431D cells were thawed and washed twice in HBSS with $Ca^{2+}$ and then resuspended at $10^6$ cells/ml in HBSS containing $Ca^{2+}$. $10^5$ cells/well were stained with either a 50% or 16% anti-Cad-11 antibody media for 45 min on ice, washed twice in HBSS containing $Ca^{2+}$ and then stained with a secondary goat anti-mouse IgG antibody conjugated with phytoerytherin at a concentration of 1% for 45 on ice and then washed again twice in HBSS containing Ca²⁺. Cells were then resuspended in 400 µl of HBSS containing Ca²⁺ and 1% formaldehyde and subsequently analyzed on a FACScalibur for PE positive cells.

Results

Anti-Cad-11 antibody-containing media from the Peptide 3 hybridomas bound to the Cad-11 EC1-2 protein and the EC1-Fc fusion protein (FIG. 28, HL vs CAD11 and HL vs Cad11-EC1, respectively), but did not bind proteins containing the EC1-2 domains of Cad-8 and MN-Cad (FIG. 28, HL vs CAD8 and HL vs MNCAD, respectively). Control hybridoma media did not bind any of the cadherin proteins (FIG. 28, Media vs CAD11, Media vs CAD8, and Media vs MNCAD).

Anti-Cad-11 antibodies from the Peptide 3 hybridomas also bound to cells expressing human Cad-11 protein (FIG. 29, see arrow), but not to non-Cad-11-expressing control cells that expressed Neos. This result confirmed the presence of anti-Cad-11 antibodies in the hybridomas that recognize both Peptide 3 and Cad-11-expressing cells in vitro.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An isolated antibody that specifically binds an EC1 domain of a mammalian Cadherin-11 protein, wherein the antibody binds an epitope comprising SEQ ID NO:11, or an epitope that is present in SEQ ID NO:12, in the EC1 domain of the mammalian Cadherin-11 protein.

2. The isolated antibody of claim 1, wherein the antibody binds an epitope that is present in SEQ ID NO:3.

3. The isolated antibody of claim 2, wherein the epitope does not include the amino acid sequence EEY.

4. The isolated antibody of claim 1, wherein the antibody is selected from the group consisting of a monoclonal antibody, a polyclonal antibody, a humanized antibody, a chimeric antibody, a single chain antibody, and an antibody fragment.

5. The isolated antibody of claim 4, wherein the antibody is an antibody fragment.

6. The isolated antibody of claim 5, wherein the antibody fragment is selected from the group consisting of an Fab, an Fab', an F(ab')$_2$ and an scFv.

7. A pharmaceutical composition comprising an antibody that specifically binds an EC1 domain of a mammalian Cadherin-11 protein, wherein the antibody binds an epitope comprising SEQ ID NO:11, or an epitope that is present in SEQ ID NO:12, in the EC1 domain of the mammalian Cadherin-11 protein.

8. The pharmaceutical composition of claim 7, wherein the antibody binds SEQ ID NO:3.

9. The pharmaceutical composition of claim 7, further comprising a disease-modifying anti-rheumatic drug.

10. The pharmaceutical composition of claim 9, wherein the disease-modifying anti-rheumatic drug is methotrexate.

11. The pharmaceutical composition of claim 7, further comprising an anti-inflammatory agent.

12. The pharmaceutical composition of claim 11, wherein the anti-inflammatory agent is an NSAID or a steroid.

13. The pharmaceutical composition of claim 11, wherein the anti-inflammatory agent is a disease modifying antirheumatic drug.

14. The isolated antibody of claim 1, wherein the antibody binds an epitope that comprises SEQ ID NO:11.

15. The isolated antibody of claim 1, wherein the antibody binds an epitope that is present in SEQ ID NO:12.

16. The pharmaceutical composition of claim 7, wherein the antibody binds an epitope that comprises SEQ ID NO:11.

17. The pharmaceutical composition of claim 7, wherein the antibody binds an epitope that is present in SEQ ID NO:12.

* * * * *

SEQUENCE LISTING

```
<160> NUMBER OF SEQ ID NOS: 13

<210> SEQ ID NO 1
<211> LENGTH: 3654
<212> TYPE: DNA
<213> ORGANISM: Homo sapiens

<400> SEQUENCE: 1
agatgccgcg ggggccgctc gcagccgccg ctgacttgtg aatgggaccg ggactggggc      60
cgggactgac accgcagcgc ttgccctgcg ccagggactg gcggctcgga ggttgcgtcc     120
accctcaagg gccccagaaa tcactgtgtt ttcagctcag cggccctgtg acattccttc     180
gtgttgtcat ttgttgagtg accaatcaga tgggtggagt gtgttacaga aattggcagc     240
aagtatccaa tgggtgaaga agaagctaac tggggacgtg ggcagccctg acgtgatgag     300
ctcaaccagc agagacattc catcccaaga gaggtctgcg tgacgcgtcc gggaggccac     360
cctcagcaag accaccgtac agttggtgga aggggtgaca gctgcattct cctgtgccta     420
ccacgtaacc aaaaatgaag gagaactact gtttacaagc cgccctggtg tgcctgggca     480
tgctgtgcca cagccatgcc tttgccccag agcggcgggg gcacctgcgg ccctccttcc     540
atgggcacca tgagaagggc aaggaggggc aggtgctaca gcgctccaag cgtggctggg     600
tctggaacca gttcttcgtg atagaggagt acaccgggcc tgaccccgtg cttgtgggca     660
ggcttcattc agatattgac tctggtgatg ggaacattaa atacattctc tcaggggaag     720
gagctggaac cattttttgtg attgatgaca aatcagggaa cattcatgcc accaagacgt     780
tggatcgaga agagagagcc cagtacacgt tgatggctca ggcggtggac agggacacca     840
atcggccact ggagccaccg tcggaattca ttgtcaaggt ccaggacatt aatgacaacc     900
ctccggagtt cctgcacgag acctatcatg ccaacgtgcc tgagaggtcc aatgtgggaa     960
cgtcagtaat ccaggtgaca gcttcagatg cagatgaccc cacttatgga aatagcgcca    1020
agttagtgta cagtatcctc gaaggacaac cctattttc ggtggaagca cagacaggta    1080
tcatcagaac agccctaccc aacatggaca gggaggccaa ggaggagtac cacgtggtga    1140
tccaggccaa ggacatgggt ggacatatgg gcggactctc agggacaacc aaagtgacga    1200
tcacactgac cgatgtcaat gacaacccac caaagttttcc gcagagcgta taccagatgt    1260
ctgtgtcaga agcagccgtc cctggggagg aagtaggaag agtgaaagct aaagatccag    1320
acattggaga aaatggctta gtcacataca atattgttga tggagatggt atggaatcgt    1380
ttgaaatcac aacggactat gaaacacagg aggggtgat aaagctgaaa agcctgtag    1440 attttgaaac caaaagagcc tatagcttga aggtagaggc agccaacgtg cacatcgacc    1500
```

```
cgaagtttat cagcaatggc cctttcaagg acactgtgac cgtcaagatc tcagtagaag   1560
atgctgatga gcccctatg ttcttggccc aagttacat ccacgaagtc caagaaaatg    1620
cagctgctgg caccgtggtt gggagagtgc atgccaaaga ccctgatgct gccaacagcc   1680
cgataaggta ttccatcgat cgtcacactg acctcgacag attttttcact attaatccag   1740 aggatggttt tattaaaact acaaaacctc tggatagaga ggaaacagcc tggctcaaca   1800
tcactgtctt tgcagcagaa atccacaatc ggcatcagga agccaaagtc ccagtggcca   1860
ttagggtcct tgatgtcaac gataatgctc ccaagtttgc tgccccttat gaaggtttca   1920
tctgtgagag tgatcagacc aagccacttt ccaaccagcc aattgttaca attagtgcag   1980
atgacaagga tgacacggcc aatggaccaa gatttatctt cagcctaccc cctgaaatca   2040
ttcacaatcc aaatttcaca gtcagagaca accgagataa cacagcaggc gtgtacgccc   2100
ggcgtggagg gttcagtcgg cagaagcagg acttgtacct tctgcccata gtgatcagcg   2160
atggcggcat cccgcccatg agtagcacca acaccctcac catcaaagtc tgcgggtgcg   2220
acgtgaacgg ggcactgctc tcctgcaacg cagaggccta cattctgaac gccggcctga   2280
gcacaggcgc cctgatcgcc atcctcgcct gcatcgtcat tctcctggtc attgtagtat   2340
tgtttgtgac cctgagaagg caaaagaaag aaccactcat tgtctttgag gaagaagatg   2400
tccgtgagaa catcattact tatgatgatg aaggggggtgg ggaagaagac acagaagcct   2460
ttgatattgc caccctccag aatcctgatg gtatcaatgg atttatcccc cgcaaagaca   2520
tcaaacctga gtatcagtac atgcctagac ctgggctccg gccagcgccc aacagcgtgg   2580
atgtcgatga cttcatcaac acgagaatac aggaggcaga caatgacccc acggctcctc   2640
cttatgactc cattcaaatc tacggttatg aaggcagggg ctcagtggcc gggtccctga   2700
gctccctaga gtcggccacc acagattcag acttggacta tgattatcta cagaactggg   2760
gacctcgttt taagaaacta gcagatttgt atggttccaa agacacttt gatgacgatt   2820 cttaacaata acgatacaaa tttggcctta agaactgtgt ctggcgttct caagaatcta   2880
gaagatgtgt aaacaggtat ttttttaaat caaggaaagg ctcatttaaa acaggcaaag   2940
ttttacagag aggatacatt taataaaact gcgaggacat caaagtggta atactgtga    3000 aataccttt ctcacaaaaa ggcaaatatt gaagttgttt atcaacttcg ctagaaaaaa   3060
aaaacacttg gcatacaaaa tatttaagtg aaggagaagt ctaacgctga actgacaatg   3120
aagggaaatt gtttatgtgt tatgaacatc caagtctttc ttcttttta agttgtcaaa    3180 gaagcttcca caaattaga aaggacaaca gttctgagct gtaatttcgc cttaaactct   3240
ggacactcta tatgtagtgc attttttaaac ttgaaatata taatattcag ccagcttaaa   3300
cccatacaat gtatgtacaa tacaatgtac aattatgtct cttgagcatc aatcttgtta   3360
ctgctgattc ttgtaaatct ttttgcttct actttcatct taaactaata cgtgccagat   3420
ataactgtct tgtttcagtg agagacgccc tatttctatg tcatttttaa tgtatctatt   3480
tgtacaattt taaagttctt attttagtat acgtataaat atcagtattc tgacatgtaa   3540
gaaaatgtta cggcatcaca cttatatttt atgaacattg tactgttgct ttaatatgag   3600
cttcaatata agaagcaatc tttgaaataa aaaagatttt tttttaaaa aaaa          3654
```

<210> SEQ ID NO 2
<211> LENGTH: 796
<212> TYPE: PRT
<213> ORGANISM: Homo sapiens

<400> SEQUENCE: 2

-continued

```
Met Lys Glu Asn Tyr Cys Leu Gln Ala Ala Leu Val Cys Leu Gly Met
  1               5                  10                  15

Leu Cys His Ser His Ala Phe Ala Pro Glu Arg Arg Gly His Leu Arg
             20                  25                  30

Pro Ser Phe His Gly His His Glu Lys Gly Lys Glu Gly Gln Val Leu
             35                  40                  45

Gln Arg Ser Lys Arg Gly Trp Val Trp Asn Gln Phe Phe Val Ile Glu
         50                  55                  60

Glu Tyr Thr Gly Pro Asp Pro Val Leu Val Gly Arg Leu His Ser Asp
 65                  70                  75                  80

Ile Asp Ser Gly Asp Gly Asn Ile Lys Tyr Ile Leu Ser Gly Glu Gly
                 85                  90                  95

Ala Gly Thr Ile Phe Val Ile Asp Asp Lys Ser Gly Asn Ile His Ala
                100                 105                 110

Thr Lys Thr Leu Asp Arg Glu Glu Arg Ala Gln Tyr Thr Leu Met Ala
             115                 120                 125

Gln Ala Val Asp Arg Asp Thr Asn Arg Pro Leu Glu Pro Pro Ser Glu
        130                 135                 140

Phe Ile Val Lys Val Gln Asp Ile Asn Asp Asn Pro Pro Glu Phe Leu
145                 150                 155                 160

His Glu Thr Tyr His Ala Asn Val Pro Glu Arg Ser Asn Val Gly Thr
                165                 170                 175

Ser Val Ile Gln Val Thr Ala Ser Asp Ala Asp Asp Pro Thr Tyr Gly
            180                 185                 190

Asn Ser Ala Lys Leu Val Tyr Ser Ile Leu Glu Gly Gln Pro Tyr Phe
        195                 200                 205

Ser Val Glu Ala Gln Thr Gly Ile Ile Arg Thr Ala Leu Pro Asn Met
    210                 215                 220

Asp Arg Glu Ala Lys Glu Glu Tyr His Val Val Ile Gln Ala Lys Asp
225                 230                 235                 240

Met Gly Gly His Met Gly Gly Leu Ser Gly Thr Thr Lys Val Thr Ile
                245                 250                 255

Thr Leu Thr Asp Val Asn Asp Asn Pro Pro Lys Phe Pro Gln Ser Val
            260                 265                 270

Tyr Gln Met Ser Val Ser Glu Ala Ala Val Pro Gly Glu Glu Val Gly
        275                 280                 285

Arg Val Lys Ala Lys Asp Pro Asp Ile Gly Glu Asn Gly Leu Val Thr
    290                 295                 300

Tyr Asn Ile Val Asp Gly Asp Gly Met Glu Ser Phe Glu Ile Thr Thr
305                 310                 315                 320

Asp Tyr Glu Thr Gln Glu Gly Val Ile Lys Leu Lys Lys Pro Val Asp
                325                 330                 335

Phe Glu Thr Lys Arg Ala Tyr Ser Leu Lys Val Glu Ala Ala Asn Val
            340                 345                 350

His Ile Asp Pro Lys Phe Ile Ser Asn Gly Pro Phe Lys Asp Thr Val
        355                 360                 365

Thr Val Lys Ile Ser Val Glu Asp Ala Asp Glu Pro Pro Met Phe Leu
    370                 375                 380

Ala Pro Ser Tyr Ile His Glu Val Gln Glu Asn Ala Ala Gly Thr
385                 390                 395                 400

Val Val Gly Arg Val His Ala Lys Asp Pro Asp Ala Ala Asn Ser Pro
                405                 410                 415
```

```
Ile Arg Tyr Ser Ile Asp Arg His Thr Asp Leu Asp Arg Phe Phe Thr
            420                 425                 430

Ile Asn Pro Glu Asp Gly Phe Ile Lys Thr Thr Lys Pro Leu Asp Arg
        435                 440                 445

Glu Glu Thr Ala Trp Leu Asn Ile Thr Val Phe Ala Ala Glu Ile His
    450                 455                 460

Asn Arg His Gln Glu Ala Lys Val Pro Val Ala Ile Arg Val Leu Asp
465                 470                 475                 480

Val Asn Asp Asn Ala Pro Lys Phe Ala Ala Pro Tyr Glu Gly Phe Ile
                485                 490                 495

Cys Glu Ser Asp Gln Thr Lys Pro Leu Ser Asn Gln Pro Ile Val Thr
            500                 505                 510

Ile Ser Ala Asp Asp Lys Asp Thr Ala Asn Gly Pro Arg Phe Ile
        515                 520                 525

Phe Ser Leu Pro Pro Glu Ile Ile His Asn Pro Asn Phe Thr Val Arg
    530                 535                 540

Asp Asn Arg Asp Asn Thr Ala Gly Val Tyr Ala Arg Arg Gly Gly Phe
545                 550                 555                 560

Ser Arg Gln Lys Gln Asp Leu Tyr Leu Leu Pro Ile Val Ile Ser Asp
                565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
        595                 600                 605

Tyr Ile Leu Asn Ala Gly Leu Ser Thr Gly Ala Leu Ile Ala Ile Leu
    610                 615                 620

Ala Cys Ile Val Ile Leu Leu Val Ile Val Val Leu Phe Val Thr Leu
625                 630                 635                 640

Arg Arg Gln Lys Lys Glu Pro Leu Ile Val Phe Glu Glu Asp Val
                645                 650                 655

Arg Glu Asn Ile Ile Thr Tyr Asp Asp Glu Gly Gly Gly Glu Glu Asp
            660                 665                 670

Thr Glu Ala Phe Asp Ile Ala Thr Leu Gln Asn Pro Asp Gly Ile Asn
        675                 680                 685

Gly Phe Ile Pro Arg Lys Asp Ile Lys Pro Glu Tyr Gln Tyr Met Pro
    690                 695                 700

Arg Pro Gly Leu Arg Pro Ala Pro Asn Ser Val Asp Val Asp Asp Phe
705                 710                 715                 720

Ile Asn Thr Arg Ile Gln Glu Ala Asp Asn Asp Pro Thr Ala Pro Pro
                725                 730                 735

Tyr Asp Ser Ile Gln Ile Tyr Gly Tyr Glu Gly Arg Gly Ser Val Ala
            740                 745                 750

Gly Ser Leu Ser Ser Leu Glu Ser Ala Thr Thr Asp Ser Asp Leu Asp
        755                 760                 765

Tyr Asp Tyr Leu Gln Asn Trp Gly Pro Arg Phe Lys Lys Leu Ala Asp
    770                 775                 780

Leu Tyr Gly Ser Lys Asp Thr Phe Asp Asp Ser
785                 790                 795

<210> SEQ ID NO 3
<211> LENGTH: 34
<212> TYPE: PRT
<213> ORGANISM: Homo sapiens

<400> SEQUENCE: 3
```

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
            20                  25                  30

Gly Asn

<210> SEQ ID NO 4
<211> LENGTH: 34
<212> TYPE: PRT
<213> ORGANISM: Homo sapiens

<400> SEQUENCE: 4

Gly Trp Val Trp Asn Gln Met Phe Val Leu Glu Glu Phe Ser Gly Pro
1               5                   10                  15

Glu Pro Ile Leu Val Gly Arg Leu His Thr Asp Leu Asp Pro Gly Ser
            20                  25                  30

Lys Lys

<210> SEQ ID NO 5
<211> LENGTH: 34
<212> TYPE: PRT
<213> ORGANISM: Homo sapeins

<400> SEQUENCE: 5

Ser Trp Val Trp Asn Gln Phe Phe Val Leu Glu Glu Tyr Thr Gly Thr
1               5                   10                  15

Asp Pro Leu Tyr Val Gly Lys Leu His Ser Asp Met Asp Arg Gly Asp
            20                  25                  30

Gly Ser

<210> SEQ ID NO 6
<211> LENGTH: 1145
<212> TYPE: DNA
<213> ORGANISM: Artificial Sequence
<220> FEATURE:
<223> OTHER INFORMATION: Cad-11-EC1-FC fusion coding sequence

<400> SEQUENCE: 6
atgaaggaga actactgttt acaagccgcc ctggtgtgcc tgggcatgct gtgccacagc      60
catgcctttg ccccagagcg gcgggggcac ctgcggccct ccttccatgg gaccatgag     120
aagggcaagg aggggcaggt gctacagcgc tccaagcgtg gctgggtctg aaccagttc     180
ttcgtgatag aggagtacac cgggcctgac ccgtgcttg tgggcaggct tcattcagat     240
attgactctg gtgatgggaa cattaaatac attctctcag gggaaggagc tggaaccatt     300
tttgtgatta tgacaaatc aggaacatt catgccacca agacgttgga tcgagaagag     360
agagcccagt acacgttgat ggctcaggcg gtggacaggg acaccaatcg ccactggag     420
ccaccgtcgg aattcattgt caaggtccag agatctgtgg agtgcccacc ttgcccagca     480
ccacctgtgg caggaccttc agtcttcctc ttccccccaa acccaagga caccctgatg     540
atctccagaa cccctgaggt cacgtgcgtg gtggtggacg tgagccacga agacccgag     600
gtccagttca ctggtacgt ggacggcatg gaggtgcata tgccaagac aaagccacgg     660
gaggagcagt caacagcac gttccgtgtg gtcagcgtcc tcaccgtcgt gcaccaggac     720
tggctgaacg gcaaggagta caagtgcaag gtctccaaca aaggcctccc agcccccatc     780
gagaaaacca tctccaaaac caagggcag ccccgagaac acaggtgta cacccctgccc     840

-continued

```
ccatcccggg aggagatgac caagaaccag gtcagcctga cctgcctggt caaaggcttc    900
taccccagcg acatcgccgt ggagtgggag agcaatgggc agccggagaa caactacaag    960
accacacctc ccatgctgga ctccgacggc tccttcttcc tctacagcaa gctcaccgtg   1020
gacaagagca ggtggcagca ggggaacgtc ttctcatgct ccgtgatgca tgaggctctg   1080
cacaaccact acacacagaa gagcctctcc ctgtctccgg gtaaatgagt gccacggcta   1140
gctgg                                                                1145

<210> SEQ ID NO 7
<211> LENGTH: 380
<212> TYPE: PRT
<213> ORGANISM: Artificial Sequence
<220> FEATURE:
<223> OTHER INFORMATION: Cad-11-EC1-Fc fusion protein

<400> SEQUENCE: 7

Met Lys Glu Asn Tyr Cys Leu Gln Ala Ala Leu Val Cys Leu Gly Met
  1               5                  10                  15

Leu Cys His Ser His Ala Phe Ala Pro Glu Arg Arg Gly His Leu Arg
             20                  25                  30

Pro Ser Phe His Gly His His Glu Lys Gly Lys Glu Gly Gln Val Leu
         35                  40                  45

Gln Arg Ser Lys Arg Gly Trp Val Trp Asn Gln Phe Phe Val Ile Glu
     50                  55                  60

Glu Tyr Thr Gly Pro Asp Pro Val Leu Val Gly Arg Leu His Ser Asp
 65                  70                  75                  80

Ile Asp Ser Gly Asp Gly Asn Ile Lys Tyr Ile Leu Ser Gly Glu Gly
                 85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Asp Thr Asn Arg Pro Leu Glu Pro Pro Ser Glu
    130                 135                 140

Phe Ile Val Lys Val Gln Arg Ser Val Glu Cys Pro Pro Cys Pro Ala
145                 150                 155                 160

Pro Pro Val Ala Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Gln Phe Asn Trp Tyr Val Asp
        195                 200                 205

Gly Met Glu Val His Asn Ala Lys Thr Lys Pro Arg Glu Glu Gln Phe
    210                 215                 220

Asn Ser Thr Phe Arg Val Val Ser Val Leu Thr Val Val His Gln Asp
225                 230                 235                 240

Trp Leu Asn Gly Lys Glu Tyr Lys Cys Lys Val Ser Asn Lys Gly Leu
                245                 250                 255

Pro Ala Pro Ile Glu Lys Thr Ile Ser Lys Thr Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300
```

```
Ile Ala Val Glu Trp Glu Ser Asn Gly Gln Pro Glu Asn Asn Tyr Lys
305                 310                 315                 320

Thr Thr Pro Pro Met Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys Val Pro Arg Leu Ala
    370                 375                 380

<210> SEQ ID NO 8
<211> LENGTH: 41
<212> TYPE: DNA
<213> ORGANISM: Artificial Sequence
<220> FEATURE:
<223> OTHER INFORMATION: primer sequence

<400> SEQUENCE: 8 ttttttttg aattcatgaa ggagaactac tgtttacaag c                     41

<210> SEQ ID NO 9
<211> LENGTH: 42
<212> TYPE: DNA
<213> ORGANISM: Artificial Sequence
<220> FEATURE:
<223> OTHER INFORMATION: primer sequence

<400> SEQUENCE: 9 tttttttta gatctctgga ccttgacaat gaattccgac gg                    42

<210> SEQ ID NO 10
<211> LENGTH: 33
<212> TYPE: PRT
<213> ORGANISM: Homo sapiens

<400> SEQUENCE: 10

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
            20                  25                  30

Gly

<210> SEQ ID NO 11
<211> LENGTH: 4
<212> TYPE: PRT
<213> ORGANISM: Homo sapiens

<400> SEQUENCE: 11

Gly Pro Asp Pro
1

<210> SEQ ID NO 12
<211> LENGTH: 19
<212> TYPE: PRT
<213> ORGANISM: Homo sapiens

<400> SEQUENCE: 12

Val Leu Val Gly Arg Leu His Ser Asp Ile Asp Ser Gly Asp Gly Asn
1               5                   10                  15

Ile Lys Tyr
```

```
<210> SEQ ID NO 13
<211> LENGTH: 37
<212> TYPE: PRT
<213> ORGANISM: Homo sapiens

<400> SEQUENCE: 13

Gly Trp Val Trp Asn Gln Phe Phe Val Ile Glu Glu Tyr Thr Gly Pro
 1               5                  10                  15

Asp Pro Val Leu Val Gly Arg Leu His Ser Asp Ile Asp Ser Gly Asp
            20                  25                  30

Gly Asn Ile Lys Tyr
        35
```